United States Patent

Sargent et al.

Patent Number: 5,753,665
Date of Patent: May 19, 1998

[54] THERAPEUTIC AGENTS

[75] Inventors: Bruce Jeremy Sargent; David John Heal, both of Nottingham, Great Britain; Maria Isabel Fernández Fernández, Madrid, Spain

[73] Assignee: Knoll Aktiengesellschaft, Ludwigshafen, Germany

[21] Appl. No.: 628,662

[22] PCT Filed: Oct. 12, 1994

[86] PCT No.: PCT/EP94/03364

§ 371 Date: Jun. 25, 1996

§ 102(e) Date: Jun. 25, 1996

[87] PCT Pub. No.: WO95/10521

PCT Pub. Date: Apr. 20, 1995

[30] Foreign Application Priority Data

Oct. 13, 1993 [GB] United Kingdom ............ 9321162

[51] Int. Cl.⁶ ............... A01N 43/54; C07D 487/00
[52] U.S. Cl. ............................. 514/258; 544/263
[58] Field of Search ..................... 544/263; 514/258

[56] References Cited

U.S. PATENT DOCUMENTS 4,269,820 5/1981 Davies et al. .................. 424/10
5,387,747 2/1995 Bru-Magniez et al. ......... 514/233.2

FOREIGN PATENT DOCUMENTS

WO89/01478 2/1989 WIPO .

*Primary Examiner*—Mukund J. Shah
*Assistant Examiner*—Tamthom T. Ngo
*Attorney, Agent, or Firm*—Keil & Weinkauf

[57] ABSTRACT

Compounds of formula (I) which includes pharmaceutically acceptable salts thereof and stereoisomers thereof:

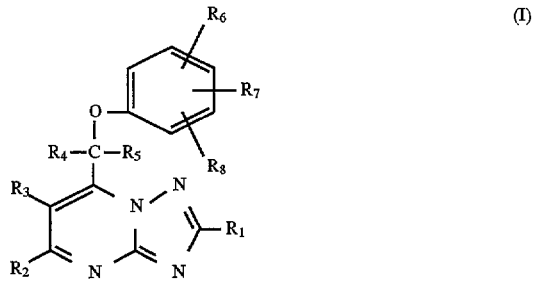

wherein: $R_1$ represents H or one of the following groups (optionally substituted with one or more of halo, cyano, hydroxy or amino): $C_{1-6}$ alkyl, $C_{1-6}$ alkoxy or $C_{1-6}$ alkanoyl; $R_2$ and $R_3$ independently represent H or one of the following groups (optionally substituted with one or more of halo, cyano, hydroxy or amino): $C_{1-6}$ alkyl, $C_{1-6}$ alkoxy or $C_{1-6}$ alkanoyl, $C_{1-6}$ alkylthio, $C_{1-6}$ alkylsulphinyl or $C_{1-6}$ alkylsulphonyl; $R_4$ and $R_5$ combined together with the carbon atom to which they are attached represent $C_{3-6}$ cycloalkylidene (each alkyl or cycloalkylidene being optionally substituted with one or more of halo, cyano, hydroxy, amino or $C_{1-6}$ alkyl); and $R_6$, $R_7$ and $R_8$ independently represent H, halo, hydroxy, mercapto, cyano or one of the following groups (optionally substituted with one or more of halo, cyano, hydroxy or amino; and any nitrogen atom being optionally substituted with one or more $C_{1-6}$ alkyl): $C_{1-6}$ alkyl, $C_{1-6}$ alkoxy or $C_{1-6}$ alkanoyl, $C_{1-6}$ alkylthio, $C_{1-6}$ alkylsulphinyl, etc; have utility in the treatment and/or prophylaxis or seizures, neurological disorders such as epilepsy and/or conditions in which there is neurological damage such as stroke, brain trauma, head injuries and haemorrhage.

12 Claims, No Drawings

THERAPEUTIC AGENTS

This is a 371 application of PCT/EP 94/03364 filed on Oct. 12, 1994.

This invention relates to derivatives of 1,2,4-triazolo[1,5-a]pyrimidines, to pharmaceutical compositions containing them, to processes for their preparation and to their use in the treatment and/or prophylaxis of seizures, neurological disorders such as epilepsy and/or conditions in which there is neurological damage such as stroke, brain trauma, head injuries and haemorrhage.

In particular the present invention provides compounds of formula I

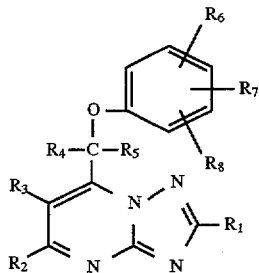

which includes pharmaceutically acceptable salts thereof and stereoisomers thereof
in which:

$R_1$ represents H or one of the following groups (optionally substituted with one or more of halo, cyano, hydroxy or amino): $C_{1-6}$alkyl, $C_{1-6}$alkoxy or $C_{1-6}$alkanoyl;

$R_2$ and $R_3$ independently represent H or one of the following groups (optionally substituted with one or more of halo, cyano, hydroxy or amino): $C_{1-6}$alkyl, $C_{1-6}$alkoxy, $C_{1-6}$alkanoyl, $C_{1-6}$alkylthio, $C_{1-6}$alkylsulphinyl or $C_{1-6}$alkylsulphonyl;

$R_4$ and $R_5$ independently represent H, $C_{1-6}$alkyl or $R_4$ and $R_5$ combined together with the carbon atom to which they are attached represent $C_{3-6}$cycloalkylidene (each alkyl or cycloalkylidene being optionally substituted with one or more of halo, cyano, hydroxy, amino or $C_{1-6}$alkyl); and $R_6$, $R_7$ and $R_8$ independently represent H, halo, hydroxy, mercapto, cyano or one of the following groups (optionally substituted with one or more of halo, cyano, hydroxy or amino; and any nitrogen atom being optionally substituted with one or more $C_{1-6}$alkyl): $C_{1-6}$alkyl, $C_{1-6}$alkanoyl, $C_{1-6}$alkoxy, $C_{2-6}$alkoxycarbonyl, carboxy, $C_{1-6}$alkanoyloxy, $C_{1-6}$alkylthio, $C_{1-6}$alkylsulphinyl, $C_{1-6}$alkylsulphonyl, $C_{1-6}$alkylsulphonylamino, sulphamoyl, carbamoyl, $C_{2-6}$alkylcarbamoyl or $C_{1-6}$alkanoylamino;

which are useful in the treatment and/or prophylaxis of seizures, neurological disorders such as epilepsy and/or conditions in which there is neurological damage such as stroke, brain trauma, head injuries and haemorrhage.

It will be understood that any group mentioned herein which contains a chain of three or more atoms signifies a group in which the chain may be straight or branched. For example, an alkyl group may comprise propyl which includes n-propyl and isopropyl and butyl which includes n-butyl, sec-butyl, isobutyl and tert-butyl. The total number of carbon atoms is specified herein for certain substituents, for example $C_{1-6}$alkyl signifies an alkyl group having from 1 to 6 carbon atoms. The term 'halo' as used herein signifies fluoro, chloro, bromo and iodo. The term 'optionally substituted' as used herein, unless immediately followed by a list of one or more substituent group or groups, means optionally substituted with one or more of halo, cyano, hydroxy, amino or $C_{1-6}$alkyl. When the phenyl ring substituents $R_6$, $R_7$ and $R_8$ are other than H, the substituent may replace any H attached to a carbon atom in the ring and may be located at any such position of the ring, ie up to three of positions 2, 3, 4, 5 and/or 6.

Pharmaceutically acceptable compounds of formula I or II may comprise those compounds which, if administered to an animal in a therapeutically effective dose, may be non-toxic and/or may be associated with limited effects in the animal to be treated that would be acceptable in the light of the nature of the therapy and/or condition to be treated; and those compounds which may be compatible with pharmaceutical carriers and/or diluents suitable for formulating the pharmaceutical compositions of the present invention described herein.

Racemic compounds of formula I in which:
$R_1$, $R_2$, $R_3$, $R_4$ and $R_8$ are all H;
$R_5$ is methyl; and either:
$R_6$ and $R_7$ are both H; or:
$R_6$ is 4-chloro and $R_7$ is H or 2-chloro;
are known.

Therefore the present invention provides novel compounds of formula II

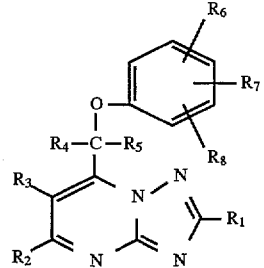

which includes pharmaceutically acceptable salts thereof and stereoisomers thereof
in which:

$R_1$ represents H or one of the following groups (optionally substituted with one or more of halo, cyano, hydroxy or amino): $C_{1-6}$alkyl, $C_{1-6}$alkoxy or $C_{1-6}$alkanoyl;

$R_2$ and $R_3$ independently represent H or one of the following groups (optionally substituted with one or more of halo, cyano, hydroxy or amino): $C_{1-6}$alkyl, $C_{1-6}$alkoxy, $C_{1-6}$alkanoyl, $C_{1-6}$alkylthio, $C_{1-6}$alkylsulphinyl or $C_{1-6}$alkylsulphonyl;

$R_4$ and $R_5$ independently represent H, $C_{1-6}$alkyl or $R_4$ and $R_5$ combined together with the carbon atom to which they are attached represent $C_{3-6}$cycloalkylidene (each alkyl or cycloalkylidene being optionally substituted with one or more of halo, cyano, hydroxy, amino or $C_{1-6}$alkyl); and $R_6$, $R_7$ and $R_8$ independently represent H, halo, hydroxy, mercapto, cyano or one of the following groups (optionally substituted with one or more of halo, cyano, hydroxy or amino; and any nitrogen atom being optionally substituted with one or more $C_{1-6}$alkyl): $C_{1-6}$alkyl, $C_{1-6}$alkanoyl, $C_{1-6}$alkoxy, $C_{2-6}$alkoxycarbonyl, carboxy, $C_{1-6}$alkanoyloxy, $C_{1-6}$alkylthio, $C_{1-6}$alkylsulphinyl, $C_{1-6}$alkylsulphonyl, $C_{1-6}$alkylsulphonylamino, sulphamoyl, carbamoyl, $C_{2-6}$alkylcarbamoyl or $C_{1-6}$alkanoylamino;

with the proviso that if
$R_1$, $R_2$, $R_3$, $R_4$ and $R_8$ are all H;
$R_5$ is methyl; and either:
$R_6$ and $R_7$ are both H; or:
$R_6$ is 4-chloro and $R_7$ is H or 2-chloro;
the compound of formula II is not a racemate.

Preferred compounds of formula I or II, are those in which:

$R_1$, $R_2$, $R_3$, $R_4$ and $R_5$ independently represent H or $C_{1-4}$alkyl; and $R_6$, $R_7$ and $R_8$ independently represent H, halo, cyano, or one of the following groups (optionally substituted with one or more halo): $C_{1-4}$alkyl, $C_{1-4}$alkoxy, $C_{1-4}$alkanoyl, $C_{1-4}$alkylthio, $C_{1-4}$alkylsulphinyl or $C_{1-4}$alkylsulphonyl.

Particularly preferred compounds of formula I or II are those in which:

$R_1$, $R_2$ and $R_3$ independently represent H or methyl;

$R_4$ and $R_5$ independently represent H, methyl or ethyl; and $R_6$, $R_7$ and $R_8$ independently represent H, fluoro, chloro, bromo, cyano, trifluoromethyl, methoxy, trifluoromethoxy, acetyl, methylthio, ethylthio, methylsulphinyl or methylsulphonyl.

Specific compounds of formula I or II are:

7-[1-(4-fluorophenoxy)ethyl]-1,2,4-triazolo[1,5-a]pyrimidine;
7-[1-(4-chlorophenoxy)ethyl]-1,2,4-triazolo[1,5-a]pyrimidine;
7-[1-(4-bromophenoxy)ethyl]-1,2,4-triazolo[1,5-a]pyrimidine;
7-[1-(4-cyanophenoxy)ethyl]-1,2,4-triazolo[1,5-a]pyrimidine;
7-[1-(4-trifluoromethylphenoxy)ethyl]-1,2,4-triazolo[1,5-a]pyrimidine;
7-[1-(4-methoxyphenoxy)ethyl]-1,2,4-triazolo[1,5-a]pyrimidine;
7-[1-(4-trifluoromethoxyphenoxy)ethyl]-1,2,4-triazolo[1,5-a]pyrimidine;
7-[1-(4-acetylphenoxy)ethyl]-1,2,4-triazolo[1,5-a]pyrimidine;
7-{1-[4-(methylthio)phenoxy]ethyl}-1,2,4-triazolo[1,5-a]pyrimidine;
7-[1-(4-methylsulphinylphenoxy)ethyl]-1,2,4-triazolo[1,5-a]pyrimidine;
7-[1-(4-methylsulphonylphenoxy)ethyl]-1,2,4-triazolo[1,5-a]pyrimidine;
7-{1-[4-(ethylthio)phenoxy]ethyl}-1,2,4-triazolo[1,5-a]pyrimidine;
7-[1-(3-chlorophenoxy)ethyl]-1,2,4-triazolo[1,5-a]pyrimidine;
7-[1-(2,4-difluorophenoxy)ethyl]-1,2,4-triazolo[1,5-a]pyrimidine;
7-[1-(2,4-dichlorophenoxy)ethyl]-1,2,4-triazolo[1,5-a]pyrimidine;
7-[1-(3,4-dichlorophenoxy)ethyl]-1,2,4-triazolo[1,5-a]pyrimidine;
7-[1-(2-chloro-4-fluorophenoxy)ethyl]-1,2,4-triazolo[1,5-a]pyrimidine;
7-[1-(4-chlorophenoxy)ethyl]-2-methyl-1,2,4-triazolo[1,5-a]pyrimidine;
7-(4-chlorophenoxymethyl)-1,2,4-triazolo[1,5-a]pyrimidine;
7-[1-(4-chlorophenoxy)-1-methylethyl]-1,2,4-triazolo[1,5-a]pyrimidine; and
7-[1-(4-chlorophenoxy)propyl]-1,2,4-triazolo[1,5-a]pyrimidine.

Specific examples of stereoisomers of formula I or II are:

(+)-7-[1-(4-fluorophenoxy)ethyl]-1,2,4-triazolo[1,5-a]pyrimidine;
(−)-7-[1-(4-fluorophenoxy)ethyl]-1,2,4-triazolo[1,5-a]pyrimidine;
(+)-7-[1-(4-chlorophenoxy)ethyl]-1,2,4-triazolo[1,5-a]pyrimidine; and
(−)-7-[1-(4-chlorophenoxy)ethyl]-1,2,4-triazolo[1,5-a]pyrimidine;

Certain compounds of formula I or II may form salts of formula I or II with organic or inorganic acids and/or bases.

As stated above, reference herein to compounds of formula I or II includes all salts of formula I or II which are pharmaceutically acceptable.

Particularly suitable salts of formula I or II which are pharmaceutically acceptable are those which may be formed from acids and, for example, comprise salts of inorganic acids (for example salts of hydrochloric, hydrobromic, hydriodic, nitric, sulphuric and/or phosphoric acids), salts of organic acids (for example salts of maleic, acetic, citric, fumaric, tartaric, succinic, benzoic, pamoic, palmitic, methylsulphuric and/or dodecanoic acids) and/or salts of acidic amino acids (for example salts of glutamic acids). Such salts include all pharmaceutically acceptable salts formed from multivalent acids (for example bicarbonate and/or orthophosphate salts).

It will be appreciated that such salts of formula I or II, provided they are pharmaceutically acceptable may be used in therapy in place of corresponding compounds of formula I or II. Such salts may be prepared by reacting corresponding compounds of formula I or II with a suitable acid or base in a conventional manner.

Certain compounds of formula I or II may exist in more than one physical form (for example different crystal forms) and the present invention includes each physical form (for example each crystal form) of compounds of formula I or II and mixtures thereof.

Certain compounds of formula I or II, may also exist in the form of solvates (for example hydrates) and the present invention includes each solvate of compounds of formula I or II and mixtures thereof. The degree of solvation may be non-stoichiometric. If the solvent is water the hydrate may be, for example, a hemihydrate, a monohydrate or a dihydrate.

It will be appreciated by those skilled in the art that certain compounds of formula I or II may contain one or more chiral centre or centres and exist in different optically active forms. Thus, for example, compounds of formula I or II in which $R_4$ and $R_5$ are different contain a chiral centre at the asymmetrically substituted carbon atom. When a compound of formula I or II contains a single chiral centre it may exist in two enantiomeric forms. The present invention includes each enantiomer of compounds of formula I or II and mixtures thereof.

The enantiomers may be obtained by methods known to those skilled in the art. Such methods typically include one or more of any of the following:

resolution via formation of diastereoisomeric salts or complexes which may be separated, for example, by crystallisation;

formation of diastereoisomeric derivatives or complexes which may be separated (for example, by crystallisation, gas-liquid or liquid chromatography), followed by the liberation of the desired enantiomer from the separated derivative;

selective derivatisation of one enantiomer by reaction with an enantiomer-specific reagent (for example enzymatic esterification, oxidation or reduction), followed by separation of the modified and unmodified enantiomers;

use of gas-liquid or liquid chromatography in a chiral environment (for example on a chiral support such as silica gel with a bound chiral ligand and/or in the presence of a chiral solvent);

asymmetric synthesis of a specific enantiomer using optically active reagents, substrates, catalysts, solvents and/or enzymatic processes; and asymmetric transformation of one enantiomer into the other.

When compounds of formula I or II contain more than one chiral centre they may exist in diastereoisomeric forms. The diastereoisomers may be separated by methods known to those skilled in the art, for example by chromatography or crystallisation and individual enantiomers within the diastereoisomers may be separated as described above. The present invention includes each diastereoisomer of compounds of formula I or II and mixtures thereof.

It will be appreciated that where the active moiety is transformed by the separation procedures described above, a further step may be required to convert the transformation product back to the active moiety.

Certain compounds of formula I or II may exist in different tautomeric forms or as different geometric isomers, and the present invention includes each tautomer and/or geometric isomer of compounds of formula I or II and mixtures thereof.

Certain compounds of formula I or II may exist in different stable conformational forms which may be separable. For example, if $R_3$, $R_4$ and/or $R_5$ are bulky groups there may be restricted rotation about one or more single bond or bonds due to steric hinderance, or if $R_4$ and $R_5$ and the carbon atom to which they are attached represent cycloalkylidene the ring may exist in more than one stable conformation. Torsional asymmetry due to restricted rotation about an asymmetric single bond, for example because of steric hindrance or ring strain, may permit separation of different conformers. The present invention includes each conformational isomer of compounds of formula I or II and mixtures thereof.

Certain compounds of formula I or II may exist in zwitterionic form and the present invention includes each zwitterionic form of compounds of formula I or II and mixtures thereof.

The present invention also relates to pharmaceutical compositions comprising a therapeutically effective amount of a compound of formula I or II together with a pharmaceutically acceptable diluent or carrier. Such pharmaceutical compositions may be used for the treatment and/or prophylaxis of the diseases, disorders and/or conditions described herein. Preferably pharmaceutical compositions of the present invention comprise the preferred and/or particularly preferred compounds of formula I or II described herein. Specific compounds which may be incorporated into the pharmaceutical compositions of the present invention are the compounds exemplified herein.

As used herein, the term "active compound" denotes one or more compound or compounds of formula I or II and mixtures thereof.

In therapeutic use, the active compound may be administered orally, rectally, parenterally or topically. Thus the therapeutic compositions of the present invention may take the form of any of the known pharmaceutical compositions for such methods of administration. The compositions may be formulated in a manner known to those skilled in the art, to give a controlled release, for example rapid release or sustained release, of the active compound. Pharmaceutically acceptable carriers suitable for use in such compositions are well known in the art of pharmacy. The compositions may contain from about 0.1% to about 99% by weight of active compound and are generally prepared in unit dosage form. Preferably the unit dosage of active compound is from about 1 mg to about 1000 mg. The excipients used in the preparation of these compositions are the excipients known in the pharmacist's art.

Preferably compositions of the present invention are administered orally in the known pharmaceutical forms for such administration. Dosage forms suitable for oral administration may comprise tablets, pills, capsules, caplets, granules, powders, extrudates, elixirs, syrups, solutions and/or suspensions (for example in aqueous and/or oily media).

Solid oral dosage forms, for example tablets, may be prepared by mixing the active compound with one or more of the following ingredients and/or mixtures thereof:

inert diluents (for example lactose, powdered sugar, pharmaceutical grade starch, kaolin, mannitol, calcium phosphate and/or calcium sulphate);

disintegrating agents (for example maize starch, methyl cellulose, agar, bentonite, cellulose, wood products, alginic acid, guar gum, citrus pulp, carboxymethylcellulose and/or sodium lauryl sulphate);

lubricating agents (for example magnesium stearate, boric acid, sodium benzoate, sodium acetate, sodium chloride, leucine and/or polyethylene glycol);

binders (for example starch, gelatin, sugars [such as sucrose, molasses and/or lactose], and/or natural and/or synthetic gums [such as acacia, sodium alginate, extract of Irish moss, carboxymethylcellulose, methylcellulose, ethylcellulose, polyethylene glycol, waxes, microcrystalline cellulose and/or polyvinylpyrrolidone]);

colouring agents (for example conventional pharmaceutically acceptable dyes);

sweetening and/or flavouring agents;

preservatives;

one or more pharmaceutically acceptable couple or couples (for example those comprising an acid and a carbonate and/or bicarbonate salt), which effervesce to aid dissolution if the solid dosage form is added to water; and other optional ingredients known in the art to permit production of oral dosage forms by known methods such as tabletting.

Solid oral dosage forms may be formulated in a manner known to those skilled in the art so as to give a sustained release of the active compound. Enteric coated, solid oral dosage forms comprising compositions of the present invention may be advantageous, depending on the nature of the active compound. Various materials, for example shellac and/or sugar, may be present as coatings, or to otherwise modify the physical form of the oral dosage form. For example tablets or pills may, if desired, be provided with enteric coatings by known methods, for example by the use of cellulose acetate phthalate and/or hydroxy propyl methylcellulose phthalate.

Capsules and/or caplets (for example hard or soft gelatin capsules) comprising the active compound (with or without added excipients such as a fatty oil), may be prepared by conventional means and, if desired, provided with enteric coatings in a known manner. The contents of the capsule and/or caplet may be formulated using known methods to give sustained release of the active compound.

Liquid oral dosage forms comprising compositions of the present invention may be an elixir, suspension and/or syrup (for example, aqueous suspensions containing the active compound in an aqueous medium in the presence of a non-toxic suspending agent [such as sodium carboxymethylcellulose] and/or oily suspensions containing the active compound in a suitable vegetable oil [such as arachis oil and/or sunflower oil]). Liquid oral dosage forms may also comprise one or more sweetening agent, flavouring agent, preservatives and/or mixtures thereof.

The active compound may be formulated into granules and/or powders with or without additional excipients. The granules and/or powders may be ingested directly by the patient or they may be added to a suitable liquid carrier (for example water) before ingestion. The granules and/or powders may contain disintegrants (for example a pharmaceutically acceptable effervescent couple formed from an acid and a carbonate and/or bicarbonate salt) to facilitate dispersion in the liquid medium.

Preferably each of the above oral dosage forms may contain from about 1 mg to about 1000 mg, more preferably from about 5 mg to about 500 mg (for example 10 mg, 50 mg, 100 mg, 200 mg, or 400 mg) of the active compound.

Compositions of the present invention may be administered rectally in the known pharmaceutical forms for such administration (for example, suppositories with hard fat, semi-synthetic glyceride, cocoa butter and/or polyethylene glycol bases).

Compositions of the present invention may also be administered parenterally (for example by intravenous injection) in the known pharmaceutical forms for such administration (for example sterile suspensions in aqueous and/or oily media and/or sterile solutions in a suitable solvent).

Pharmaceutical compositions of the present invention may be administered topically, the compositions comprising a matrix in which the active compound is dispersed so that the active compound is held in contact with the skin in order to administer the compound transdermally. The amount of active compound comprising a topical formulation should be such that a therapeutically effective amount of the active compound would be delivered during the period of time which the topical formulation is intended to be on the skin.

A suitable transdermal composition may be prepared by mixing or dispersing the active compound in a topical vehicle together with a potential transdermal accelerant such as dimethyl sulphoxide and/or propylene glycol. The topical vehicle may be a pharmaceutically acceptable foam, paste, salve, lotion, cream, ointment, emulsion and/or gel base; and/or a composition suitable for application in the form of a spray. Topical vehicles may also comprise topical delivery devices such as cataplasms, poultices, patches and/or impregnated bandages.

A suitable cream may be prepared by incorporating the active compound in petrolatum and/or light liquid paraffin which is then dispersed in an aqueous medium using surfactants. An ointment may be prepared by mixing the active compound with a mineral oil, petrolatum and/or a wax (such as paraffin wax and/or beeswax). A gel may be prepared by mixing the active compound with a gelling agent (such as basified Carbomer BP) in the presence of water. A clear gel may comprise a clarifying agent (for example a denaturated alcohol [such as denaturated ethanol]).

Preferably pharmaceutical compositions of the present invention for topical administration may also comprise a thickening agent and/or may further comprise a pH adjusting agent that is compatible with the active compound. Preferably the pH adjusting agent is present in an amount which is sufficient to activate the thickening agent, if present, and which will keep the pH of the composition within a pharmaceutically and cosmetically acceptable range that will not damage the skin. More preferably the pH of the composition is from about 5.0 to about 9.0.

If pharmaceutical composition of the present invention for topical administration is an emulsion, such an emulsion may be either an oil-in-water or a water-in-oil emulsion. The oil phase of such an emulsion may comprise one or more of the following ingredients: hydrocarbon oils, waxes, natural oils, silicone oils, fatty acid esters, fatty alcohols and/or mixtures thereof. Pharmaceutical compositions of the present invention that are emulsions can be prepared by using an emulsifier or mixture of emulsifiers for use in water-in-oil or oil-in-water emulsions and acceptable for use in topical pharmaceutical compositions. Such emulsifiers may comprise any suitable emulsifier or emulsifiers well known to those skilled in the art and/or mixtures thereof.

When a pharmaceutical composition of the present invention for topical administration is not an emulsion, an emulsifying ingredient or surfactant may still be present as a surface active agent to promote greater therapeutic activity in the pharmaceutical composition when it is applied topically.

Pharmaceutical compositions of the present invention for topical administration may additionally comprise another component or components well known to those skilled in the art for example: emulsion stabilisers, emulsion stabilising salts, sequestrants, emollients, humectants, moisturisers, film formers, perfumes, preservatives, colourings and/or mixtures thereof.

The active compound may also be administered by continuous infusion either from an external source (for example by intravenous infusion) or from a source of the active compound placed within the body. Internal sources include implanted reservoirs containing the active compound to be infused from which the active compound is continuously released (for example by osmosis) or implants. Implants may be liquid such as a suspension or solution in a pharmaceutically acceptable solvent of the active compound to be infused (for example in the form of a very sparingly water-soluble derivative such as a dodecanoate salt and/or ester in an oil). Implants may also be solid in the form of an implanted support (for example a synthetic resin and/or waxy material) for the active compound to be infused. The support may be a single body containing all the active compound or a series of several bodies each containing part of the active compound to be delivered. The amount of active compound present in an internal source should be such that a therapeutically effective amount of the active compound is delivered over a long period of time.

In some formulations it may be beneficial to use the active compound, or pharmaceutical compositions containing the active compound, in the form of particles of very small size, for example as obtained by fluid energy milling.

In the compositions of the present invention described herein the active compound may, if desired, be associated with other compatible pharmacologically active ingredients.

An aspect of the present invention comprises use of the active compound and/or a pharmaceutical composition or compositions comprising a therapeutically effective amount of the active compound in a method of therapy for animals. As used herein the term animal is to be construed as including human beings. Preferred patients for the therapy described herein comprise mammals, more preferably human beings.

Compounds of formula I or II are indicated for therapeutic use as medicaments for the treatment, prophylaxis and/or inhibition of seizures, neurological disorders such as epilepsy, and/or conditions in which there is neurological damage, such as stroke, brain trauma, head injuries and haemorrhage. The therapeutic activity of compounds falling within the disclosure of formula I has been demonstrated by means of various in vivo pharmacological tests in standard laboratory animals. Such tests include those tests of anticonvulsant activity in m ice described below.

It will be appreciated that the term therapy as used herein includes both treatment and/or prophylactic use of the active compound and one or more pharmaceutical composition or compositions comprising a therapeutically effective amount of the active compound. For example, in the present invention prophylactic use of the active compound comprises prevention of the onset of seizures, and/or neurological disorders such as epilepsy, and/or use as neuroprotective agents to protect against conditions in which there is neurological damage, such as stroke, brain trauma, head injuries and haemorrhage, in animals including human beings.

Accordingly, a further aspect of the present invention provides a method of treatment and/or prophylaxis of seizures, neurological disorders such as epilepsy and conditions in which there is neurological damage, such as stroke, brain trauma, head injuries and haemorrhage, in animals including human beings, which comprises the administration to a patient in need thereof a therapeutically effective amount of the active compound and/or one or more pharmaceutical composition or compositions containing a therapeutically effective amount of the active compound.

While the precise mechanism of action of the active compound is unknown at present, it is believed that the pharmacological activity of the active compound in the conditions outlined herein may arise from the ability to potentiate transmission of the neurotransmitter gamma-amino butyric acid (GABA-A) and/or the ability to activate potassium ion ($K^+$) channels in neurones. Therefore, another aspect of the present invention comprises a method of treatment as described herein in which the active compound is a potentiator of GABA-A transmission and/or an activator of neuronal $K^+$ channels. However, the present invention should not be considered limited to the active compound having such pharmacological activity.

Whilst the precise amount of the active compound administered in the therapeutic methods outlined above will depend on a number of factors (for example the severity of the condition, the age and/or past medical history of the patient) and always lies within the sound discretion of the administering pharmacist, physician and/or veterinary, a suitable daily dose of the active compound for administration to human beings, is generally from about 1 mg to about 1000 mg, more usually from about 5 mg to about 500 mg, given in a single dose or in divided doses at one or more times during the day. Oral administration is preferred.

The active compound may be used in adjunctive therapy with one or more other compound or compounds having activity in the treatment and/or prophylaxis of seizures, neurological disorders such as epilepsy, and/or conditions in which there is neurological damage, such as stroke, brain trauma, head injuries and haemorrhage, in animals including human beings. The active compound and/or one or more pharmaceutical composition or compositions comprising a therapeutically effective amount of the active compound may be used to provide a local and/or systemic therapeutic effect.

A still further aspect of the present invention provides use of the active compound in the preparation of a medicament. Preferably the medicament is useful in the treatment and/or prophylaxis of seizures, neurological disorders such as epilepsy and conditions in which there is neurological damage, such as stroke, brain trauma, head injuries and haemorrhage, in animals including human beings.

Processes for the preparation of compounds of formula I or II will now be described. These processes form a further aspect of the present invention.

Compounds of formula I or II may be prepared by reacting of compounds of formula III

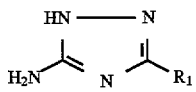
III with compounds of formula IV

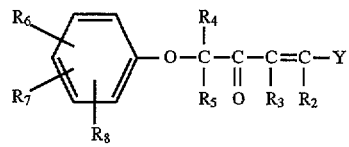
IV in which Y is a suitable leaving group, for example Cl, —N(Me)$_2$ or alkoxy.

Compounds of formula I or II may be prepared by reacting compounds of formula V

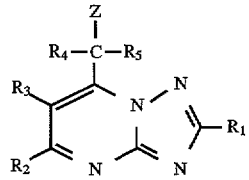
V in which Z is a suitable leaving group, for example Br or Cl, with anions of formula VI

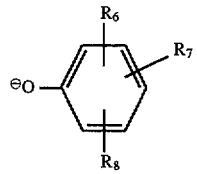
VI

Compounds of formula IV in which Y is —N(Me)$_2$ may be prepared by reacting compounds of formula VII

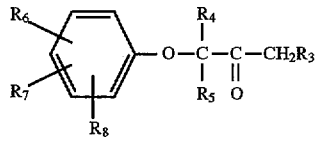
VII with compounds of formula VIII

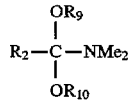
VIII in which R$_9$ and R$_{10}$ independently represent C$_{1-6}$alkyl, or if R$_2$ is H, with 'Gold's reagent' which is a compound of formula Me$_2$NCH=NCH=NMe$_2$Cl.

Compounds of formula V may be prepared by reacting compounds of formula III with compounds of formula IX

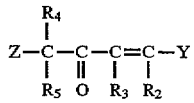
IX

Compounds of formula IX in which Y is —N(Me)$_2$ may be prepared by reacting compounds of formula ZCR$_4$R$_5$COCH$_2$R$_3$ with compounds of formula VIII, or if R$_2$ is H, with Gold's reagent.

Compounds of formula V in which Z is halo, may be prepared by reacting compounds of formula X

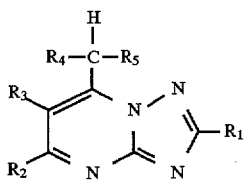

with a halogenating agent, for example N-bromosuccinimide.

Compounds of formula X may be prepared by reacting compounds of formula III with compounds of formula XI

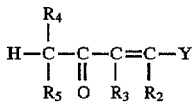

Compounds of formula XI in which Y is —N(Me)$_2$ may be prepared by reacting compounds of formula CHR$_4$R$_5$COCH$_2$R$_3$ with compounds of formula VIII, or if R$_2$ is H, with Gold's reagent.

Compounds of formula X in which R$_1$ is other than H, may be prepared by reacting compounds of formula XII

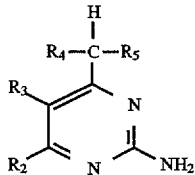

with compounds of formula R$_1$CN→O to form an intermediate and cyclising the intermediate using a suitable acid catalyst.

Compounds of formula X may be prepared by reacting compounds of formula XIII

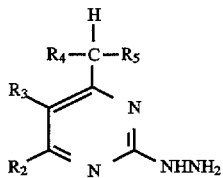

with carboxylic acids of formula R$_1$CO$_2$H or compounds of formula R$_1$C(OR$_{11}$)$_3$ in which R$_{11}$ is methyl or ethyl.

Compounds of formula X in which R$_3$ is H may be prepared by decarboxylating acids of formula XIV

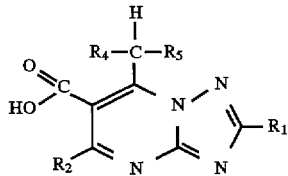

using, for example, heat and/or a suitable acid catalyst.

Compounds of formula XIV may be prepared by hydrolysing esters of formula XV

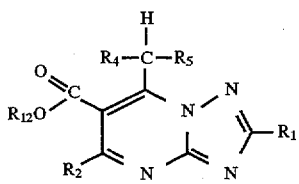

in which R$_{12}$ is optionally substituted alkyl or optionally substituted aryl.

Compounds of formula XV may be prepared by reacting compounds of formula III with compounds of formula XVI

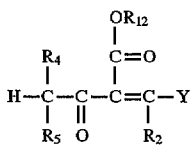

Compounds of formula XVI in which Y is —N(Me)$_2$ may be prepared by reacting compounds of formula CHR$_4$R$_5$COCHR$_3$CO$_2$R$_{12}$ with compounds of formula VIII, or if R$_2$ is H, with Gold's reagent.

Compounds of formula I or II may be prepared by coupling alcohols of formula XVII

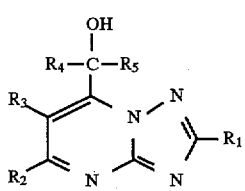

with phenols of formula XVIII

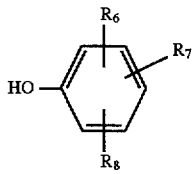

in the presence of a coupling agent which, for example, in the 'Mitsunobu' reaction is diethylazodicarboxylate with triphenylphosphine.

If R$_4$ and R$_5$ are different the stereospecific 'Mitsunobu' reaction provides a route to single enantiomers of compounds of formula I or II.

Compounds of formula V in which Z is halo, may be prepared by reacting alcohols of formula XVII with a halogenating agent, for example thionyl chloride; or triphenylphosphine with bromine.

Alcohols of formula XVII in which R$_5$ is H may be prepared by reducing compounds of formula XIX

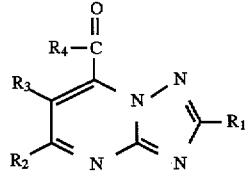

with a reducing agent, for example sodium borohydride, or optionally with a chiral reducing agent to afford single enantiomers of alcohols of formula XVII.

Compounds of formula XIX may be prepared by using a cleaving agent to cleave compounds of formula XX

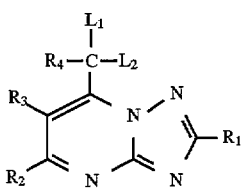

XX in which $L_1$ and $L_2$ are alkoxy or alkylthio; or together with the carbon atom to which they are attached represent a dioxolane, dioxane, dithiolane or dithiane ring. For example when compounds of formula XX are dithiolanes or dithianes the cleaving agent may be silver nitrate with N-chlorosuccinimide; or ceric ammonium nitrate. When $L_1$ and $L_2$ are both methoxy the cleaving agent may be a suitable Amberlyst® ion exchange resin available commercially from Aldrich Chemicals.

Compounds of formula X in which $R_5$ is H, may be prepared by reducing of compounds of formula XIX.

Compounds of formula XX may be prepared by reacting compounds of formula III with compounds of formula XXI

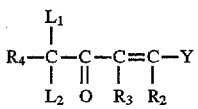

XXI

Compounds of formula XXI in which Y is —$N(Me)_2$ may be prepared by reacting compounds of formula XXII

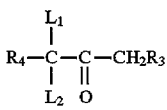

XXII with compounds of formula VIII, or if $R_2$ is H, with Gold's reagent.

Alcohols of formula XVII may be prepared by reacting compounds of formula V with hydroxide ions, for example using a suitable alkali.

Alcohols of formula XVII may be prepared by hydrolysing compounds of formula XXIII

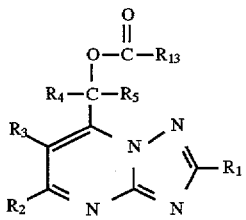

XXIII in which $R_{13}$ is optionally substituted alkyl or optionally substituted aryl with, for example, potassium carbonate. The hydrolysis may be conducted under conditions which afford single enantiomers of alcohols of formula XVII, for example by use of an appropriate hydrolytic enzyme.

Compounds of formula XXIII may be prepared by reacting compounds of formula V with carboxylate anions of formula $R_{13}CO_2^-$, which may be any acylate group (for example acetate or benzoate); and may also be a chiral group (for example mandelate [$PhCH(OH)CO_2^-$]). If single enantiomers of $R_{13}CO_2^-$ are used to prepare compounds of formula XXIII in which $R_4$ and $R_5$ are different, mixtures of diasteromeric esters may be formed, which may be separated (for example by selective recrystallisation) and the desired diastereoisomers hydrolysed to afford single enantiomers of alcohols of formula XVII.

Compounds of formula XXIII may be prepared by reacting compounds of formula XVII with carboxylic acids of formula $R_{13}CO_2H$ in the presence of a coupling agent, for example dicyclohexylcarbodiimide; or triphenylphosphine with diethylazodicarboxylate.

Compounds of formula XXIII may be prepared by reacting compounds of formula III with compounds of formula XXIV

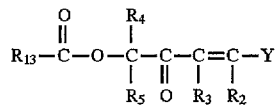

XXIV

Compounds of formula XXIV in which Y is —$N(Me)_2$ may be prepared by reacting compounds of formula XXV

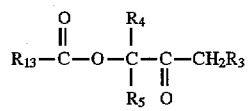

XXV with compounds of formula VIII, or if $R_2$ is H, with Gold's reagent.

Compounds of formula XXV may be prepared by reacting compounds of formula XXVI

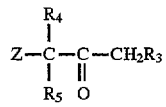

XXVI with anions of formula $R_{13}CO_2^-$.

Compounds of formula I or II in which $R_1$ is other than H, may be prepared by reacting compounds of formula XXVII

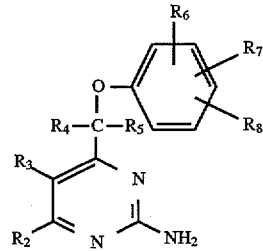

XXVII with compounds of formula $R_1CN \rightarrow O$ to form an intermediate and cyclising the intermediate using a suitable acid catalyst.

Compounds of formula I or II, in which at least one of $R_6$, $R_7$ and/or $R_8$ is selected from alkylsulphinyl and alkylsulphonyl, may be prepared by oxidising compounds of formula I or II in which $R_6$, $R_7$ and/or $R_8$ are alkylthio, using, for example, peracetic acid or 3-chloroperbenzoic acid.

Compounds of formula I or II in which $R_3$ is H may be prepared by decarboxylating acids of formula XXVIII

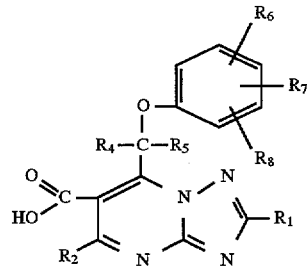

XXVIII using, for example, heat and/or suitable acid catalyst.

If $R_4$ and $R_5$ are different this provides routes to single enantiomers of compounds of formula I or II.

Compounds of formula XXVIII may be prepared by hydrolysing of esters of formula XXIX

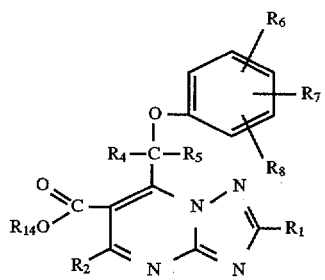
XXIX in which $R_{14}$ is optionally substituted alkyl or optionally substituted aryl.

Compounds of formula XXIX may be prepared by reacting compounds of formula III with compounds of formula XXX

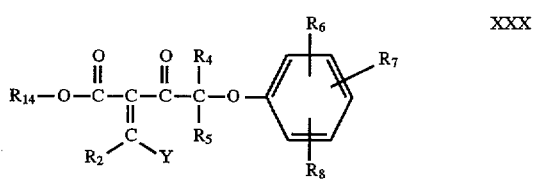
XXX

Compounds of formula XXX may be prepared by reacting compounds of formula VIII with compounds of formula XXXI

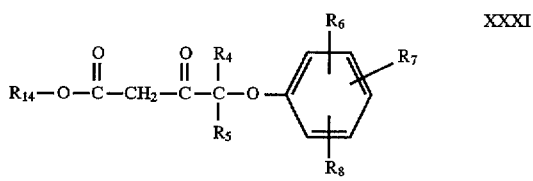
XXXI

Compounds of formula I or II in which $R_3$ is H may be prepared by reducing compounds of formula XXXII

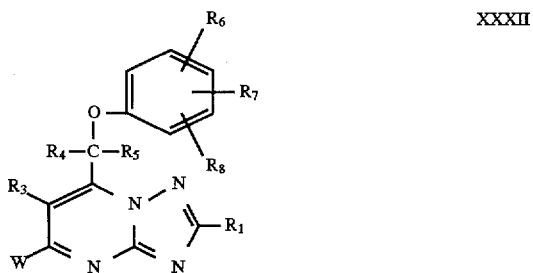
XXXII in which W is a suitable leaving group, for example halo, using a reducing agent. If W is halo, the reducing agent may be, for example, hydrogen optionally in the presence of a catalyst, for example, palladium.

If $R_4$ and $R_5$ are different this provides routes to single enantiomers of compounds of formula I or II.

Compounds of formula XXXII in which W is halo, may be prepared by reacting compounds of formula XXXII in which W is hydroxy with a halogenating agent, for example phosphoryl chloride.

Compounds of formula XXXII in which $R_3$ is H and W is hydroxy may be prepared by reacting compounds of formula III with compounds of formula XXXI.

The anticonvulsant activity of compounds of formula I or II was demonstrated by the following pharmacological tests.

The first test involved observing the ability of the compound of formula I or II to antagonise myoclonic seizures induced in mice by the administration of (+)-bicuculline (see Buckett W. R.; J. Pharmacol. Meth.; 1981; 5; 35–41). Bicuculline, a selective gamma-amino butyric acid-A (GABA-A) receptor antagonist, induces a characteristic convulsive syndrome when administered intravenously. The syndrome can be prevented by anti-epileptic drugs known to potentiate GABA neuro-transmission. Hereinafter, this test is referred to as 'BICM'.

In the BICM experiments groups of female mice in the weight range 25 to 30 grammes were used. Two hours prior to the experiment food was withdrawn, but the mice continued to have free access to water. The mice were divided into two groups, a control group and a test group to which compounds of formula I or II would be administered. The control group received an oral dose of 10 ml/kg of a vehicle of 1% aqueous methyl cellulose solution. The test group received orally, suspended in the same dose of the methylcellulose vehicle, a compound of formula I or II at a dose of either 100 mg/kg for initial testing or, if enough compound was available, at a range of doses to determine an $ED_{50}$ (see below). One hour after administration of all drugs (+)-bicuculline at a dose of 0.55 mg/kg was administered intravenously into a tail vein to all the mice in both groups. Such a dose of (+)-bicuculline would generally be expected to induce a seizure in the mice.

During the following two minutes each group of mice was observed, the number of mice in each group exhibiting convulsions was recorded and thus the percentage of mice in the test group in which seizures had been inhibited was determined. The greater the anticonvulsant activity of the compound of formula I or II, the higher was the percentage recorded in the BICM test. If results at more than one dose were available, then a value for the dose inhibiting the seizures in 50% of the mice ($ED_{50}$) was calculated from the regression straight line plot of the percentage of mice in which seizures were inhibited against the dose of the compound of formula I or II administered.

The second test of anticonvulsant activity involved observing the ability of a compound of formula I or II to inhibit seizures in mice induced by a maximal electroshock. Hereinafter, this test is referred to as 'MESM'.

In the MESM experiments, groups of male mice in the weight range 25 to 30 grammes had free access to food and water until the start of the experiment. The mice were divided into two groups, a control group and a test group to which compound of formula I or II would be administered. The control group received an oral dose of 10 ml/kg of a vehicle of 1% aqueous methyl cellulose solution. The test group received orally, suspended in the same dose of the methylcellulose vehicle, a compound of formula I or II at a dose of either 100 mg/kg for initial testing or, if enough compound was available, at a range of doses to determine an $ED_{50}$ (see below). One hour after administration of all drugs an electroshock of duration 1.0 second was administered to all the mice in both groups through ear clip electrodes moistened with saline. The electroshock had an intensity of 99 mA, frequency of 50 Hz and pulse width of 0.4 ms. Such a shock would generally be expected to induce a seizure in the mice.

During the following two minutes the mice in each group were observed, the number of mice in each group exhibiting tonic hind limb extension was recorded and thus the percentage of mice in which seizures had been inhibited was determined. The greater the anticonvulsant activity of the compound of formula I or II, the higher was the percentage recorded in the MESM test.

If results at more than one dose were available, then a value for the dose inhibiting seizures in 50% of the mice (ED$_{50}$) was calculated from the regression straight line plot of the percentage of mice in which seizures were inhibited against the dose of the compound of formula I or II administered.

The compounds of formula I or II described hereinafter in Examples 1 to 25a have been found to have anticonvulsant activity in at least one of the BICM and/or MESM tests.

The invention will now be illustrated by the following non-limiting examples. The final product of each example was characterised using one or more of the following techniques: elemental analysis; infra-red spectroscopy; nuclear magnetic resonance spectroscopy; gas-liquid chromatography; and liquid chromatography. Temperatures are given in degrees Celsius.

EXAMPLE 1

4-Fluorophenol (1.12 g) was added to a stirred suspension of sodium hydride (0.48 g) in dry 1,2-dimethoxyethane (35 ml). The mixture was stirred at room temperature for 30 minutes, then a solution of 7-(1-bromoethyl)-1,2,4-triazolo[1,5-a]pyrimidine (2.27 g, prepared in a similar manner to that described in Example 6 below) in dry 1,2-dimethoxyethane (85 ml) was added dropwise. The mixture was stirred at room temperature for 24 hours. The sodium bromide was removed from the mixture by filtration. The solvent was evaporated from the filtrate and the residue dissolved in dichloromethane and washed with 200 ml of a 5% aqueous solution of sodium hydroxide, followed by water. The organic layer was dried over magnesium sulphate. Evaporation of the solvent afforded a crude product which was purified by column chromatography on silica gel using as eluent a mixture of petroleum ether and ethyl acetate (in the ratio 6:4 respectively), followed by recrystallisation from a mixture of ethyl acetate and hexane, to give 7-[1-(4-fluorophenoxy)ethyl]-1,2,4-triazolo[1,5-a]-pyrimidine. Yield 1.03 g, (mp 106°–108° C.).

The ED$_{50}$, in the BICM test described above, for this compound was 13.9 mg/kg.

The ED$_{50}$, in the MESM test also described above, for this compound was 21.4 mg/kg.

EXAMPLE 2

A mixture of 3-(4-chlorophenoxy)-2-butanone (34.50 g) and N,N-dimethylformamide dimethylacetal (20.70 g) was heated under argon in an oil bath at 120° C. for 13 hours. The methanol produced in the reaction was removed under reduced pressure and the residual oil triturated with n-hexane. The solid was collected by filtration and washed with cold diethyl ether to give 4-(4-chlorophenoxy)-1-(dimethylamino)-1-penten-3-one. Yield 32.50 g.

A solution of 4-(4-chlorophenoxy)-1-(dimethylamino)-1-penten-3-one (9.80 g) in glacial acetic acid (50 ml) was added to a stirred solution of 3-amino-1,2,4-triazole (3.25 g) in glacial acetic acid (50 ml). The mixture was heated under reflux for 5 hours and then cooled to room temperature. The mixture was then poured into 300 ml of ice-water and extracted with toluene. The toluene extracts were washed with a 10% aqueous solution of sodium hydrogen carbonate, followed by water, then dried over anhydrous magnesium sulphate and the solvent was evaporated under reduced pressure. The residue was triturated with cold diethyl ether and the solid was collected by filtration and recrystallised from a mixture of ethyl acetate and petroleum ether (b.p. 40°–60° C.), to give 7-[1-(4-chlorophenoxy)ethyl]-1,2,4-triazolo[1,5-a]pyrimidine. Yield 6.91 g, (mp 111°–112° C.).

The ED$_{50}$, in the BICM test described above, for this compound was 12.7 mg/kg.

The ED$_{50}$, in the MESM test also described above, for this compound was 64.1 mg/kg.

EXAMPLE 3

A solution of 4-bromophenol (1.73 g) in dry 1,2-dimethoxyethane was added slowly to a stirred suspension of sodium hydride (0.48 g) in dry 1,2-dimethoxyethane (35 ml). The mixture was stirred for 30 minutes, then a solution of 7-(1-bromoethyl)-1,2,4-triazolo[1,5-a]pyrimidine (2.27 g, prepared in a similar manner to that described in Example 6 below) in dry 1,2-dimethoxyethane (85 ml) was added dropwise. The reaction mixture was stirred for 1 hour 30 minutes at room temperature. The sodium bromide was removed from the mixture by filtration. The solvent was evaporated from the mixture and the residue was dissolved in dichloromethane and washed with 200 ml of a 5% aqueous solution of sodium hydroxide followed by water. The organic layer was dried over magnesium sulphate. Evaporation of the solvent afforded a crude product which was purified by column chromatography on silica gel using as eluent a mixture of ethyl acetate and petroleum ether (in the ratio 4:6 respectively), followed by recrystallisation from a mixture of ethyl acetate and hexane, to give 7-[1-(4-bromophenoxy)ethyl]-1,2,4-triazolo[1,5-a]pyrimidine. Yield 2.28 g, (m.p. 121°–124° C.).

The ED$_{50}$, in the BICM test described above, for this compound was 18.9 mg/kg.

The ED$_{50}$, in the MESM test also described above, for this compound was 73.7 mg/kg.

EXAMPLE 4

A solution of 4-cyanophenol (1.19 g) in dry 1,2-dimethoxyethane was added slowly to a stirred suspension of sodium hydride (0.48 g) in dry 1,2-dimethoxyethane (35 ml). The mixture was stirred for 30 minutes, then a solution of 7-(1-bromoethyl)-1,2,4-triazolo[1,5-a]pyrimidine (2.27 g, prepared in a similar manner to that described in Example 6 below) in dry 1,2-dimethoxyethane (85 ml) was added dropwise. The reaction mixture was stirred overnight at room temperature. The sodium bromide was removed from the mixture by filtration. The solvent was evaporated from the mixture and the residue was dissolved in dichloromethane and washed with 200 ml of a 5% aqueous solution of sodium hydroxide followed by water. The organic layer was dried over magnesium sulphate. Evaporation of the solvent afforded a crude product which was purified by column chromatography on silica gel using as eluent a mixture of ethyl acetate and petroleum ether (in the ratio 6:4 respectively), followed by recrystallisation from ethyl acetate, to give 7-[1-(4-cyanophenoxy)ethyl]-1,2,4-triazolo[1,5-a]pyrimidine. Yield 1.07 g, (m.p. 163°–164° C.).

The percentage free from seizures, in the MESM test described above, for this compound was 60% at a dosage of 100 mg/kg.

EXAMPLE 5

4-Trifluoromethylphenol (1.62 g) was added to a stirred suspension of sodium hydride (0.48 g) in dry 1,2-dimethoxyethane (35 ml). The mixture was stirred at room temperature for 30 minutes, then a solution of 7-(1-bromoethyl)-1,2,4-triazolo[1,5-a]pyrimidine (2.27 g, prepared in a similar manner to that described in Example 6 below) in dry 1,2-dimethoxyethane (85 ml) was added dropwise. The mixture was stirred at room temperature for 24 hours. The sodium bromide was removed from the mixture by filtration. The solvent was evaporated from the filtrate and the residue dissolved in dichloromethane and washed with 200 ml of a 5% aqueous solution of sodium hydroxide followed by water. The organic layer was dried over magnesium sulphate. Evaporation of the solvent afforded a crude product which was purified by column chromatography on silica gel using as eluent a mixture of petroleum ether and ethyl acetate (in the ratio 6:4 respectively), followed by recrystallisation from hexane, to give 7-[1-(4-trifluoromethylphenoxy)ethyl]-1,2,4-triazolo[1,5-a]pyrimidine. Yield 1.1 g, (mp 100°–102° C.).

The $ED_{50}$, in the BICM test described above, for this compound, was 29.8 mg/kg.

The $ED_{50}$, in the MESM test also described above, for this compound was 52.1 mg/kg.

EXAMPLE 6

A mixture of 3-amino-1,2,4-triazole (11.74 g) and 1-chloro-1-penten-3-one (16.5 g) in acetic acid (225 ml) was heated under reflux for 45 minutes. The reaction mixture was cooled, poured onto ice and extracted with dichloromethane. The organic layer was dried and the solvent was evaporated under reduced pressure to give 7-ethyl-1,2,4-triazolo[1,5-a]pyrimidine. Yield 11.72 g.

A mixture of 7-ethyl-1,2,4-triazolo[1,5-a]pyrimidine (10.5 g), N-bromosuccinimide (12.63 g), dibenzoylperoxide (0.3 g) and tetrachloromethane (270 ml) was heated under reflux for 5 hours with stirring. The mixture was filtered and a crude product was obtained by evaporation of the solvent from the filtrate. This was purified by recrystallisation from tetrachloromethane to give 7-(1-bromoethyl)-1,2,4-triazolo[1,5-a]pyrimidine. Yield 10.8 g.

A solution of 4-methoxyphenol (1.24 g) in dry 1,2-dimethoxyethane was added slowly to a stirred suspension of sodium hydride (0.48 g) in dry 1,2-dimethoxyethane (35 ml). The mixture was stirred for 30 minutes, then a solution of 7-(1-bromoethyl)-1,2,4-triazolo[1,5-a]pyrimidine (2.27 g) in dry 1,2-dimethoxyethane (85 ml) was added dropwise. The reaction mixture was stirred overnight at room temperature, filtered and the solvent was evaporated from the filtrate under reduced pressure. The residue was purified by flash chromatography using as eluent a mixture of ethyl acetate and petroleum ether, followed by recrystallisation from a mixture of ethyl acetate and hexane, to give 7-[1-(4-methoxyphenoxy)ethyl]-1,2,4-triazolo[1,5-a]pyrimidine. Yield 1.67 g (mp 112°–114° C.)

The $ED_{50}$, in the BICM test described above, for this compound was 93.3 mg/kg.

EXAMPLE 7

A solution of 4-trifluoromethoxyphenol (1.78 g) in dry 1,2-dimethoxyethane was added slowly to a stirred suspension of sodium hydride (0.48 g) in dry 1,2-dimethoxyethane (35 ml). The mixture was stirred for 30 minutes, then a solution of 7-(1-bromoethyl)-1,2,4-triazolo[1,5-a] pyrimidine (2.27 g, prepared in a similar manner to that described in Example 6 above) in dry 1,2-dimethoxyethane (85 ml) was added dropwise. The reaction mixture was stirred for 4 hours at room temperature. The sodium bromide was removed from the mixture by filtration. The solvent was evaporated from the mixture and the residue was dissolved in dichloromethane and washed with 200 ml of a 5% aqueous solution of sodium hydroxide followed by water. The organic layer was dried over magnesium sulphate. Evaporation of the solvent afforded a crude product which was purified by column chromatography on silica gel using as eluent a mixture of petroleum ether and ethyl acetate (in the ratio 6:4 respectively), followed by recrystallisation from a mixture of ethyl acetate and hexane to give 7-[1-(4-trifluoromethoxyphenoxy)ethyl]-1,2,4-triazolo[1,5-a] pyrimidine. Yield 2.69 g, (m.p. 91°–93° C.).

The $ED_{50}$, in the BICM test, described above, for this compound was 11.4 mg/kg.

The $ED_{50}$, in the MESM test, also described above, for this compound was 52.8 mg/kg.

EXAMPLE 8

A solution of 4-hydroxyacetophenone (1.36 g) in dry 1,2-dimethoxyethane was added slowly to a stirred suspension of sodium hydride (0.48 g) in dry 1,2-dimethoxyethane (35 ml). The mixture was stirred for 30 minutes, then a solution of 7-(1-bromoethyl)-1,2,4-triazolo[1,5-a] pyrimidine (2.27 g, prepared in a similar manner to that described in Example 6 above) in dry 1,2-dimethoxyethane (85 ml) was added dropwise. The reaction mixture was stirred at room temperature for 24 hours. The sodium bromide was removed from the mixture by filtration. The solvent was evaporated from the mixture and the residue was dissolved in dichloromethane and washed with 200 ml of a 5% aqueous solution of sodium hydroxide followed by water. Evaporation of the solvent afforded a crude product which was recrystallised from ethyl acetate, to give 7-[1-(4-acetylphenoxy)ethyl]-1,2,4-triazolo[1,5-a]pyrimidine. Yield 0.87 g, (m.p. 136°–138° C.).

The $ED_{50}$, in the BICM test described above, for this compound was 105.8 mg/kg.

EXAMPLE 9

A solution of 4-(methylthio)phenol (2.80 g) in dry 1,2-dimethoxyethane was added slowly to a stirred suspension of sodium hydride (0.87 g) in dry 1,2-dimethoxyethane (50 ml). The mixture was stirred for 30 minutes, then a solution of 7-(1-bromoethyl)-1,2,4-triazolo[1,5-a]pyrimidine (4.54 g, prepared in a similar manner to that described in Example 6 above) in dry 1,2-dimethoxyethane (150 ml) was added dropwise. The reaction mixture was stirred overnight at room temperature. The sodium bromide was removed from the mixture by filtration. The solvent was evaporated from the mixture and the residue was dissolved in dichloromethane and washed with 200 ml of a 5% aqueous solution of sodium hydroxide followed by water. The organic layer was dried over magnesium sulphate. Evaporation of the solvent afforded a crude product which was purified by column chromatography on silica gel using as eluent a mixture of ethyl acetate and petroleum ether (in the ratio 4:6 respectively), followed by recrystallisation from a mixture of ethyl acetate and hexane, to give 7-{1-[4-(methylthio)phenoxy]ethyl}-1,2,4-triazolo[1,5-a] pyrimidine. Yield 3.66 g, (m.p. 84°–86° C.).

The percentage free from seizures, in the BICM test described above, for this compound was 50% at a dosage of 100 mg/kg.

EXAMPLE 10

A solution of 3-chloroperbenzoic acid (0.63 g) in dichloromethane (30 ml) was added dropwise at −78° C. to a stirred solution of 7-{1-[4-(methylthio)phenoxy]ethyl}-1,2, 4-triazolo[1,5-a]pyrimidine (0.89 g, prepared in a similar manner to that described in Example 9) in dichloromethane (30 ml). The reaction mixture was stirred at −78° C. for 2 hours, washed with a 10% aqueous solution of sodium hydrogen carbonate followed by water. The organic layer was dried and the solvent was evaporated under reduced pressure. The residue was purified by flash chromatography using as eluent a mixture of dichloromethane and ethanol (in the ratio of 95:5 respectively), followed by recrystallisation from a mixture of ethyl acetate and hexane, to give 7-[1-(4-methylsulphinylphenoxy)ethyl]-1,2,4-triazolo[1,5-a] pyrimidine. Yield 0.76 g, (m.p. 89°–102° C.).

The percentage free from seizures, in the BICM test described above, for this compound was 60% at a dosage of 100 mg/kg.

EXAMPLE 11

A solution of 3-chloroperbenzoic acid (2.13 g) in dichloromethane (50 ml) was added dropwise at room temperature to a stirred solution of 7-{1-[4-(methylthio)phenoxy]ethyl}-1,2,4-triazolo[1,5-a]pyrimidine (1.2 g, prepared in a similar manner to that described in Example 9) in dichloromethane (70 ml). The reaction mixture was stirred for 3 hours, then washed with a 10% aqueous solution of sodium hydrogen carbonate followed by water. The organic layer was dried and the solvent was evaporated under reduced pressure. The residue was purified by flash chromatography using ethyl acetate as eluent, followed by recrystallisation from ethanol, to give 7-[1-(4-methylsulphonylphenoxy)ethyl]-1,2,4-triazolo[1,5-a]pyrimidine. Yield 0.72 g, (m.p. 163°–164° C.).

The percentage free from seizures, in the BICM test described above, for this compound was 60% at a dosage of 100 mg/kg.

EXAMPLE 12

A solution of 4-(ethylthio)phenol (1.54 g) in dry 1,2-dimethoxyethane was added slowly to a stirred suspension of sodium hydride (0.48 g) in dry 1,2-dimethoxyethane (35 ml). The mixture was stirred for 30 minutes, then a solution of 7-(1-bromoethyl)-1,2,4-triazolo[1,5-a]pyrimidine (2.27 g, prepared in a similar manner to that described in Example 6 above) in dry 1,2-dimethoxyethane (85 ml) was added dropwise. The reaction mixture was stirred overnight at room temperature. The sodium bromide was removed from the mixture by filtration. The solvent was evaporated from the mixture and the residue dissolved in dichloromethane and washed with 200 ml of a 5% aqueous solution of sodium hydroxide followed by water. The organic layer was dried over magnesium sulphate. Evaporation of the solvent afforded a crude product which was purified by column chromatography on silica gel using as eluent a mixture of diethylether and ethyl acetate (in the ratio 6:4 respectively), followed by recrystallisation from a mixture of ethyl acetate and hexane, to give 7-{1-[4-(ethylthio)phenoxy]ethyl}-1,2,4-triazolo[1,5-a]pyrimidine. Yield 2.28 g, (m.p. 65°–67° C.).

The $ED_{50}$, in the BICM test described above, for this compound was 48.9 mg/kg.

EXAMPLE 13

A solution of 3-chlorophenol (1.28 g) in dry 1,2-dimethoxyethane was added slowly to a stirred suspension of sodium hydride (0.48 g) in dry 1,2-dimethoxyethane (35 ml). The mixture was stirred for 30 minutes, then a solution of 7-(1-bromoethyl)-1,2,4-triazolo[1,5-a]pyrimidine (2.27 g, prepared in a similar manner to that described in Example 6) in dry 1,2-dimethoxyethane (85 ml) was added dropwise. The reaction mixture was stirred overnight at room temperature, filtered and the solvent was evaporated from the filtrate under reduced pressure. The residue was purified by flash chromatography using as eluent a mixture of ethyl acetate and petroleum ether to give 7-[1-(3-chlorophenoxy)ethyl]-1,2,4-triazolo[1,5-a]pyrimidine. Yield 2.11 g, (mp 124°–126° C.).

The percentage free from seizure, in the BICM test described above, for this compound was 78% at a dosage of 100 mg/kg.

The percentage free from seizure, in the MESM test also described above, for this compound was 60% at a dosage of 100 mg/kg.

EXAMPLE 14

A solution of 2,4-difluorophenol (1.30 g) in dry 1,2-dimethoxyethane was added slowly to a stirred suspension of sodium hydride (0.48 g) in dry 1,2-dimethoxyethane (35 ml). The mixture was stirred for 30 minutes, then a solution of 7-(1-bromoethyl)-1,2,4-triazolo[1,5-a]pyrimidine (2.27 g, prepared in a similar manner to that described in Example 6) in dry 1,2-dimethoxyethane (85 ml) was added dropwise. The reaction mixture was stirred overnight at room temperature. The sodium bromide was removed from the mixture by filtration. The solvent was evaporated from the mixture and the residue was dissolved in dichloromethane and washed with 200 ml of a 5% aqueous solution of sodium hydroxide followed by water. Evaporation of the solvent afforded a crude product which was purified by column chromatography on silica gel using as eluent a mixture of dichloromethane and ethanol (in the ratio 97:3 respectively), followed by recrystallisation from a mixture of ethyl acetate and hexane, to give 7-[1-(2,4-difluorophenoxy)ethyl]-1,2,4-triazolo[1,5-a]pyrimidine. Yield 1.8 g, (m.p. 96°–97° C.).

The $ED_{50}$, in the BICM test described above, for this compound was 37.5 mg/kg.

EXAMPLE 15

A mixture of 3-(2,4-dichlorophenoxy)-2-butanone (4.66 g) and N,N-dimethylformamide dimethylacetal (2.38 g) was heated under argon in an oil bath at 120° C. for 11 hours. The methanol produced in the reaction was removed under reduced pressure and the residue was triturated with n-hexane. The solid was collected by filtration and washed with cold diethyl ether to give 4-(2,4-dichlorophenoxy)-1-(dimethylamino)-1-penten-3-one. Yield 4.07 g.

A solution of 4-(2,4-dichlorophenoxy)-1-(dimethylamino)-1-penten-3-one (2.9 g) in glacial acetic acid (25 ml) was added to a stirred solution of 3-amino-1,2,4-triazole (0.93 g) also in glacial acetic acid (25 ml). The mixture was heated under reflux for 5 hours and then cooled to room temperature. The mixture was then poured into 200 ml of ice-water and extracted with toluene. The toluene extracts were washed with a 10% aqueous solution of sodium hydrogen carbonate followed by water, then dried over anhydrous magnesium sulphate and the solvent was evaporated under reduced pressure. The residue was triturated with cold diethyl ether and the solid was collected by filtration, followed by recrystallisation from a mixture of ethyl acetate and petroleum ether (b.p. 40°–60° C.) to give 7-[1-(2,4-dichlorophenoxy)ethyl]-1,2,4-triazolo[1,5-a]pyrimidine. Yield 2.02 g, (mp 137°–138° C.).

The $ED_{50}$, in the BICM test described above, for this compound was 39.7 mg/kg.

The $ED_{50}$, in the MESM test also described above, for this compound was 109.7 mg/kg.

EXAMPLE 16

A solution of 3,4-dichlorophenol (1.22 g) in dry 1,2-dimethoxyethane was added slowly to a stirred suspension of sodium hydride (0.33 g) in dry 1,2-dimethoxyethane (30 ml). The mixture was stirred for 30 minutes, then a solution of 7-(1-bromoethyl)- 1,2,4-triazolo[1,5-a]pyrimidine (1.68 g, prepared in a similar manner to that described in Example 6) in dry 1,2-dimethoxyethane (60 ml) was added dropwise. The reaction mixture was stirred overnight at room temperature. The sodium bromide was removed from the mixture by filtration. The solvent was evaporated from the mixture and the residue was dissolved in dichloromethane and washed with 200 ml of a 5% aqueous solution of sodium hydroxide followed by water. The organic layer was dried over magnesium sulphate.

Evaporation of the solvent afforded a crude product which was purified by column chromatography on silica gel using as eluent a mixture of ethyl acetate and petroleum ether (in the ratio 4:6 respectively), followed by recrystallisation from a mixture of ethyl acetate and hexane, to give 7-[1-(3,4-dichlorophenoxy)ethyl]-1,2,4-triazolo[1,5-a] pyrimidine. Yield 1.45 g, (m.p. 146°–149° C.).

The percentage free from seizures, in the BICM test described above, for this compound was 50% at a dosage of 100 mg/kg.

EXAMPLE 17

A mixture of 2-chloro-4-fluorophenol (0.65 g) and sodium hydride (210 mg) in dry 1,2-dimethoxyethane (15 ml) was stirred at room temperature for 30 minutes. A solution of 7-(1-bromoethyl)-1,2,4-triazolo[1,5-a]pyrimidine (1 g, prepared in a similar manner to that described in Example 6) in 1,2-dimethoxyethane (35 ml) was added dropwise to the stirred mixture. The mixture was stirred at room temperature for 21 hours, then was filtered and the solvent was evaporated from the filtrate under reduced pressure. The residue was dissolved in dichloromethane, washed with a 5% aqueous solution of sodium hydroxide followed by water, dried over anhydrous magnesium sulphate and the solvent was evaporated under reduced pressure. The solid residue was purified by flash chromatography on silica gel using as eluent a mixture of ethyl acetate and petroleum ether (in the ratio 1:1), followed by recrystallisation from a mixture of ethyl acetate and hexane, to give 7-[1-(2-chloro-4-fluorophenoxy)ethyl]-1,2,4-triazolo[1,5-a]pyrimidine. Yield 0.99 g, (m.p. 89°–91° C.).

The percentage free from seizures, in the BICM test described above, for this compound was 50% at a dosage of 100 mg/kg.

The $ED_{50}$, in the MESM test described above, for this compound was 66.0 mg/kg.

EXAMPLE 18

A solution of 4-(4-chlorophenoxy)-1-(dimethylamino)-1-penten-3-one (1.58 g, prepared in a similar manner to that described in Example 2 above) in glacial acetic acid (5 ml) was added to a stirred solution of 3-amino-5-methyl-1,2,4-triazole (0.62 g) in glacial acetic acid (10 ml). The mixture was heated under reflux for 2 hours and 30 minutes and then cooled to room temperature. The mixture was then poured into ice-water (50 ml) and extracted with toluene. The toluene extracts were washed with a 10% aqueous solution of sodium hydrogen carbonate followed by water, then dried over anhydrous magnesium sulphate and the solvent was evaporated under reduced pressure. The residue was triturated with cold diethyl ether and the solid was collected by filtration, followed by recrystallisation from a mixture of ethyl acetate and petroleum ether (b.p. 40°–60° C.), to give 7-[1-(4-chlorophenoxy)ethyl]-2-methyl-1,2,4-triazolo [1,5-a]pyrimidine. Yield 1.13 g, (mp 138° C.).

The $ED_{50}$, in the BICM test described above, for this compound was 78.2 mg/kg.

The $ED_{50}$, in the MESM test also described above, for this compound was 107.7 mg/kg.

EXAMPLE 19

1,4-Dichloro-1-buten-3-one (10.9 g) (prepared in a manner analogous to the preparation of 1-chloro-4-methyl-1-penten-3-one described in Example 20 below), 3-amino-1,2,4-triazole (6.5 g) and glacial acetic acid were heated under reflux for 1 hour and 30 minutes. The reaction mixture was poured onto ice and extracted with dichloromethane. The organic layer was dried over magnesium sulphate and the solvent was evaporated to give a solid. The crude product was purified by flash chromatography using as eluent a mixture of dichloromethane and ethanol (in the ratio 97:3 respectively), followed by recrystallisation from tetrachloromethane, to give 7-chloromethyl-1,2,4-triazolo [1,5-a]pyrimidine. Yield 10.15 g.

4-Chlorophenol (2.18 g), sodium methoxide (0.92 g) and dry methanol (150 ml) were heated under reflux whilst stirring for 1 hour. The solvent was evaporated under reduced pressure. 7-Chloromethyl-1,2,4-triazolo[1,5-a] pyrimidine (2.8 g) and dry 1,2-dimethoxyethane (170 ml) were added to the crude reaction mixture. The mixture was heated under reflux whilst stirring for 10 hours. The solvent was evaporated under reduced pressure and the crude product purified by flash chromatography using ethyl acetate as eluent, followed by recrystallisation from ethyl acetate, to give 7-(4-chlorophenoxymethyl)-1,2,4-triazolo[1,5-a] pyrimidine. Yield 0.26 g, (mp 193°–194° C.).

The percentage free from seizure, in the BICM test described above, for this compound was 70% at a dosage of 100 mg/kg.

EXAMPLE 20

Anhydrous aluminium chloride (27.2 g) was added to a stirred solution of 2-methylpropionyl chloride (23.4 g) in dry trichloromethane (100 ml) with external cooling to between 0° C. and 15° C. Over a period of 1 hour chloroethene (20 g) was passed through the mixture held at 24°–26° C., after which stirring was continued for a further 40 minutes. The reaction mixture was then poured onto crushed ice, the organic layer was separated, dried over magnesium sulphate and distilled under reduced pressure to obtain a colourless liquid of 1,1-dichloro-4-methyl-3-pentanone. Yield 23 g.

1,1-Dichloro-4-methyl-3-pentanone (12.53 g) was mixed with sodium hydrogen carbonate (6.23 g) and water (30 ml). The mixture was heated under reflux for 4 hours then cooled and extracted with trichloromethane. The organic layer was dried over magnesium sulphate and distilled under reduced pressure to obtain a colourless liquid of 1-chloro-4-methyl-1-penten-3-one. Yield 5.93 g.

A mixture of 1-chloro-4-methyl-1-penten-3-one (5.83 g), 3-amino-1,2,4-triazole (3.69 g) and glacial acetic acid was heated under reflux for 1 hour and 30 minutes. The reaction mixture was poured onto ice and extracted with dichloromethane. The organic layer was dried over magnesium sulphate and the solvent was evaporated to give a product which was recrystallised from petroleum ether (b.p. 100°–140° C.), to give 7-(1-methylethyl)-1,2,4-triazolo[1,5-a]pyrimidine. Yield 4.18 g.

A mixture of 7-(1-methylethyl)-1,2,4-triazolo[1,5-a]pyrimidine (4.18 g), N-bromosuccinimide (4.59 g), and dibenzoylperoxide (70 mg) in tetrachloromethane (105 ml) was stirred and heated under reflux for 11 hours. The mixture was filtered and the solvent was removed from the filtrate to give 7-(1-bromo-1-methylethyl)-1,2,4-triazolo[1,5-a]pyrimidine. Yield 2.94 g.

A mixture of 7-(1-bromo-1-methylethyl)-1,2,4-triazolo[1,5-a]pyrimidine (2.95 g, prepared in a similar manner to that described above), 4-chlorophenol (1.56 g), sodium bicarbonate (1 g), nickel acetyl acetone (5 mg) and dry toluene (80 ml) was stirred and heated under reflux for 7 days. The solvent was evaporated and the crude product was purified by flash chromatography using as eluent a mixture of toluene and ethylacetate (in the ratio 5:1 respectively), followed by recrystallisation from n-hexane, to give 7-[1-(4-chlorophenoxy)-1-methylethyl]-1,2,4-triazolo[1,5-a]pyrimidine. Yield 0.67 g, (mp 132°–135° C.).

The $ED_{50}$, in the MESM test described above, for this compound was 45.0 mg/kg.

EXAMPLE 21

A solution of 3-chloro-2-pentanone (10 g) in acetone (50 ml) was added dropwise to a stirred mixture of 4-chlorophenol (11 g), potassium bicarbonate (20 g) and potassium iodide (1 g) in acetone (100 ml). After the addition was completed the mixture was heated under reflux for 6 hours. The mixture was then filtered, washed with acetone and the acetone was evaporated under reduced pressure. The residue was dissolved in ether (150 ml), and the ethereal mixture was washed with 300 ml of a 10% aqueous solution of sodium hydroxide followed by 300 ml of water. The mixture was then dried over magnesium sulphate. The solvent was evaporated and the residue was distilled under reduced pressure to give 3-(4-chlorophenoxy)-2-pentanone (10.96 g).

A mixture of 3-(4-chlorophenoxy)-2-pentanone (10.96 g) and N,N-dimethylformamide dimethylacetal (6 g) was heated under argon in an oil bath at 120° C. for 24 hours. The methanol produced in the reaction was removed under reduced pressure and the residual oil of 4-(4-chlorophenoxy)-1-(dimethylamino)-1-hexen-3-one (12.71 g) was used directly in the next step.

A solution of 4-(4-chlorophenoxy)-1-(dimethylamino)-1-hexen-3-one (12.67 g) in glacial acetic acid (75 ml) was added to a stirred solution of 3-amino-1,2,4-triazole (3.78 g) in glacial acetic acid (75 ml). The solution was heated under reflux for 2 hours and then poured into water (200 ml). After extraction with toluene, the organic phase was washed with a 10% aqueous solution of sodium hydrogen carbonate followed by water, dried over anhydrous magnesium sulphate and the solvent was evaporated under reduced pressure. The residue was triturated with cold diethyl ether and the solid was collected by filtration, followed by recrystallisation from a mixture of ethyl acetate and hexane to give 7-[1-(4-chlorophenoxypropyl)]-1,2,4-triazolo[1,5-a]pyrimidine. Yield 4.54, (m.p. 108°–109° C.).

The $ED_{50}$, in the BICM test described above, for this compound was 38.6 mg/kg.

The $ED_{50}$, in the MESM test also described above, for this compound was 79.4 mg/kg.

EXAMPLE 22

Racemic 7-[1-(4-fluorophenoxy)ethyl]-1,2,4-triazolo[1,5-a]pyrimidine (30 g, prepared in a similar manner to that described in Example 1) was resolved into its separate enantiomers by high performance liquid chromatography (HPLC) on a chiralcel (type OD) column of internal dimensions 50 cm×10 cm eluted with a 1:1 mixture of isohexane and isopropanol to give (+)-7-[1-(4-fluorophenoxy)ethyl]1,2,4-triazolo[1,5-a]pyrimidine as the first eluted fraction. It had an optical purity of greater than 99% and specific rotation $[\alpha]_D^{\pi}$ of +116.5° (C=1; methanol). Yield 10 g, (m.p. 100°–102° C.).

The $ED_{50}$, in the BICM test described above, for this compound was 48.3 mg/kg.

The $ED_{50}$, in the MESM test also described above, for this compound was 56.9 mg/kg.

EXAMPLE 23

(−)-7-[1-(4-Fluorophenoxy)ethyl]-1,2,4-triazolo[1,5-a]pyrimidine was isolated as the second eluted fraction from racemic 7-[1-(4-fluorophenoxy)ethyl]-1,2,4-triazolo[1,5-a]pyrimidine using HPLC (in a similar method to that described in Example 22 above). It had an optical purity of greater than 99% and a specific rotation $[\alpha]_D^{\pi}$ of −118.1° (C=1; methanol). Yield 9.5 g (m.p. 100°–102° C.).

The $ED_{50}$, in the BICM test described above, for this compound was 12.7 mg/kg.

The $ED_{50}$, in the MESM test also described above, for this compound was 79.8 mg/kg.

EXAMPLE 24

Racemic 7-[1-(4-chlorophenoxy)ethyl]-1,2,4-triazolo[1,5-a]pyrimidine (5 g, prepared in a similar manner to that described in Example 2) was resolved into its separate enantiomers by high performance liquid chromatography (HPLC) on a Chiralcel (type OD) column of internal dimensions 50 cm×10 cm eluted with a 1:1 mixture of isohexane and isopropanol to give (+)-7-[1-(4-chlorophenoxy)ethyl]-1,2,4-triazolo[1,5-a]pyrimidine as the first eluted fraction. It had an optical purity of greater than 99% and specific rotation $[\alpha]_D^{\pi}$ of +133.7°. Yield 1.8 g, (mp 98°–99° C.).

The $ED_{50}$, in the BICM test described above, for this compound was 28.1 mg/kg.

The $ED_{50}$, in the MESM test also described above, for this compound was 80.8 mg/kg.

The following Examples 24a and 24b, describe other methods of preparing (+)-7-[1-(4-chlorophenoxy)ethyl]-1,2,4-triazolo[1,5-a]pyrimidine.

EXAMPLE 24a 7-(1-Bromoethyl)-1,2,4-triazolo[1,5-a]pyrimidine (9.8 g, prepared in a similar manner to that described in Example 6 above), (R)-mandelic acid (32.8 g), triethylamine (30 ml) and dioxan (500 ml) were mixed together and heated on a steam bath for 2 hours and 30 minutes. The mixture was cooled and the solvent was evaporated under reduced pressure. The solid residue was dissolved in ethyl acetate (400 ml) and then washed with water (300 ml). The aqueous washings were extracted with ethyl acetate (200 ml) and the organic layer washed with water (200 ml), followed by triethylamine (10 ml), further water (100 ml) and brine (100 ml). The organic layer was dried over magnesium sulphate, heated with active carbon, filtered and the solvent evaporated from the filtrate to give 10.75 g of a mixture of 2 diastereoisomers: (+)-1-(1,2,4-triazolo[1,5-a]pyrimidin-7-yl)ethyl(R)-mandelate and (−)-1-(1,2,4-triazolo[1,5-a]pyrimidin-7-yl)ethyl(R)-mandelate.

The mixture of the 2 diastereoisomers (obtained as described above) was subjected to a process of fractional crystallisation using ethyl acetate as solvent. Two fractions were obtained, a first fraction of the less polar diastereciso-mer (2.8 g), and a second fraction of the more polar diastereoisomer (3.3 g).

The less polar diastereoisomer (0.7 g, prepared as above), potassium carbonate (1.4 g), water (10 ml) and methanol (25 ml) were stirred for 2 hours at ambient temperature. The solution was diluted with water (100 ml) and continuously extracted with dichloromethane overnight. The extracts were dried over magnesium sulphate and the solvent was evaporated to afford (+)-1-(1,2,4-triazolo[1,5-a]pyrimidin-7-yl)ethanol. Yield 0.27 g.

A mixture of (+)-1-(1,2,4-triazolo[1,5-a]pyrimidin-7-yl) ethanol (0.27 g), diethylazodicarboxylate (0.29 g), triphenylphosphine (0.44 g) and 4-chlorophenol (0.22 g) in dry tetrahydrofuran (40 ml) was stirred at ambient temperature for 2 days. Further diethylazodicarboxylate (0.15 g) and triphenylphosphine (0.22 g) was added to the solution, which was stirred overnight until the reaction was complete. The solvent was removed under reduced pressure and the residue was dissolved in ethyl acetate (100 ml). This solution was washed with 1M sodium hydroxide (40 ml) followed by brine (20 ml) and the solvent was evaporated. The residue was purified by flash chromatography on silica gel using as eluent a mixture of triethylamine and ethyl acetate (in the ratio 1:100 respectively) to give (+)-7-[1-(4-chlorophenoxy)ethyl]-1,2,4-triazolo[1,5-a]pyrimidine. Yield 0.33 g.

EXAMPLE 24b

A mixture of 3-chlorobutanone (10.6 g), benzoic acid (15.0 g), triethylamine (30 ml) and acetonitrile (100 ml) was heated under reflux for 1 hour 30 minutes. The mixture was cooled and filtered to remove precipitated triethylamine hydrochloride. The acetonitrile was removed from the filtrate under reduced pressure and the residue dissolved in ethyl acetate and washed with water. The organic extracts were dried over magnesium sulphate, filtered over active carbon and the solvent was removed from the filtrate under reduced pressure, to give a yellow oil of 3-benzoyloxybutan-2-one. Yield 16.7 g. The oil was used directly without further purification in the next step.

A mixture of 3-benzoyloxybutan-2-one (15.5 g) and dimethylformamide dimethylacetal (14.4 g) was heated on a steam bath for 2 hours 30 minutes. The solvent was removed from the mixture under reduced pressure. Petroleum ether (b.p. 60°–80° C.) was added to the residue, with shaking and the ether layer separated from an insoluble red oil. Further petroleum ether was added to the oil with shaking and excess ether was removed under reduced pressure to give a red-brown oil which partially crystallised on standing overnight. Petroleum ether was added and the solid was collected by filtration and washed with petroleum ether to give a yellow crystalline solid of 4-benzoyloxy-1-dimethylamino-1-penten-3-one. Yield 5.6 g. The solid was used directly without further purification in the next step.

A mixture of aminotriazole (1.78 g) and 4-benzoyloxy-1-dimethyl-amino-1-penten-3-one (5.0 g) in acetic acid (25 ml) was heated under reflux for 1 hour 30 minutes. The mixture was poured onto ice, neutralised with solid sodium bicarbonate and extracted with ethyl acetate (200 ml). The organic extracts were dried over magnesium sulphate, filtered and the solvent was removed from the filtrate under reduced pressure. Ether was added to the solid residue which was collected by filtration to give a pale brown solid of 1-(1,2,4-triazolo[1,5-a]pyrimidin-7-yl)ethyl benzoate. Yield 3.8 g.

A mixture of 1-(1,2,4-triazolo[1,5-a]pyrimidin-7-yl)ethyl benzoate (1 g), potassium carbonate (2 g), methanol (25 ml) and water (20 ml) was stirred at ambient temperature for 1 hour 30 minutes. The methanol was removed from the mixture under reduced pressure and the mixture was then diluted with brine (20 ml) before being continuously extracted with dichloromethane overnight. The extracts were dried over magnesium sulphate and the solvent evaporated under reduced pressure to give 1-(1,2,4-triazolo[1,5-a]pyrimidin-7-yl)ethanol. Yield 0.39 g.

A solution of 1-(1,2,4-triazolo[1,5-a]pyrimidin-7-yl) ethanol (1 g, prepared in an similiar manner to that described above) in dichloromethane (30 ml) was added dropwise over 30 minutes to a solution of thionyl chloride (0.5 ml) in dichloromethane (50 ml), heated under reflux, and the heating was continued for a further 2 hours. Further thionyl chloride (0.5 ml) was added and the heating continued overnight. The dichloromethane was removed by distillation and the residue dissolved in further dichloromethane (50 ml). The solution was washed with a mixture of water (20 ml) with 1M sodium bicarbonate (3 ml), and the aqueous washings were extracted with dichloromethane (20 ml). The dichloromethane solutions were combined, washed with brine (40 ml), dried over magnesium sulphate and the solvent was evaporated to give, as a light brown solid, 7-(1-chloroethyl)-1,2,4-triazolo[1,5-a]pyrimidine. Yield 1.00 g.

Triethylamine (3.81 ml) was added to a mixture of R-mandelic acid (4.16 g) in dry acetonitrile (50 ml, dried over a 4 Å molecular sieve). After 5 minutes this mixture was added to 7-(1-chloroethyl)-1,2,4-triazolo[1,5-a] pyrimidine (0.90 g). The mixture was heated under reflux overnight and the solvent was evaporated under reduced pressure at 60° C. The residue was extracted with ethyl acetate (100 ml) and water (50 ml). The ethyl acetate layer was washed with a mixture of water (20 ml) with 1M sodium bicarbonate (3 ml) followed by brine (20 ml). The solution was dried over magnesium sulphate and the solvent was removed under reduced pressure at 60° C. to give as a product 1.33 g of a mixture of the two diastereoisomers: (+)-1-(1,2,4-triazolo[1,5-a]pyrimidin-7-yl)ethyl(R)-mandelate and (−)-1-(1,2,4-triazolo[1,5-a]pyrimidin-7-yl) ethyl(R)-mandelate.

The less polar diastereoisomer may be isolated by fractional crystallisation and converted to (+)-7-[1-(4-chlorophenoxy)ethyl]-1,2,4-triazolo[1,5-a]pyrimidine [via (+)-1-(1,2,4-triazolo[1,5-a]pyrimidin-7-yl)ethanol] in a similar manner to that described in Example 24a above.

EXAMPLE 25

(−)-7-[1-(4-Chlorophenoxy)ethyl]-1,2,4-triazolo [1,5-a] pyrimidine was isolated as the second eluted fraction from racemic 7-[1-(4-chlorophenoxy)ethyl]-1,2,4-triazolo[1,5-a] pyrimidine using HPLC (in a similar method to that described in Example 24 above). It had an optical purity of greater than 98% and a specific rotation $[\alpha]_D^{rt}$ of −132.6°. Yield 1.9 g, (mp 99°–100° C.).

The $ED_{50}$, in the BICM test described above, for this compound was 9.4 mg/kg.

The $ED_{50}$, in the MESM test also described above, for this compound was 77.2 mg/kg.

The following Example 25a, describes another method of preparing (−)-7-[1-(4-chlorophenoxy)ethyl]-1,2,4-triazolo[1,5-a]pyrimidine.

EXAMPLE 25a

A solution in ethyl acetate of a mixture of the two diastereoisomers (+) and (−) 1-(1,2,4-triazolo[1,5-a]pyrimidin-7-yl)ethyl(R)-mandelate (10.75 g, prepared in a similar manner to that described in Example 24a or 24b) was subject to fractional crystallisation to give two fractions, a first fraction of the less polar diastereoisomer (2.8 g) and a second fraction of the more polar diastereoisomer (3.3 g).

The more polar diastereoisomer (0.7 g, obtained from the second fraction described above), potassium carbonate (1.61 g), water (10 ml) and methanol (25 ml) were stirred for 1 hour and 30 minutes and the methanol was evaporated. The mixture was diluted with water (50 ml) and then continuously extracted with dichloromethane for 2 hours. The extracts were dried over magnesium sulphate and the solvent was evaporated to give (−)-1-(1,2,4-triazolo[1,5-a]pyrimidin-7-yl)ethanol (0.28 g).

A mixture of (−)-1-(1,2,4-triazolo[1,5-a]pyrimidin-7-yl)ethanol (0.27 g), diethylazodicarboxylate (0.44 g), triphenylphosphine (0.68 g) and 4-chlorophenol (0.22 g) in dry tetrahydrofuran (20 ml) was stood overnight at ambient temperature until the reaction was complete. The solvent was removed under reduced pressure and the residue dissolved in ethyl acetate (100 ml). The solution was washed with 1M sodium hydroxide (40 ml) followed by brine (20 ml), and the solvent was evaporated. The residue was purified by flash chromatography on silica gel using as eluent a mixture of triethylamine and ethyl acetate (in the ratio 1:100 respectively) to give (−)-7-[1-(4-chlorophenoxy)ethyl]-1,2,4-triazolo[1,5-a]pyrimidine. Yield 0.26 g.

PHARMACEUTICAL EXAMPLES

EXAMPLE U

Tablets may be prepared from the following ingredients.

|  | Parts by Weight |
| --- | --- |
| Active compound | 10 |
| Lactose | 190 |
| Maize starch | 22 |
| Polyvinylpyrrolidone | 10 |
| Magnesium stearate | 3 |

The active compound, the lactose and some of the starch may be de-aggregated, blended and the resulting mixture may be granulated with a solution of the polyvinylpyrrolidone in ethanol. The dry granulate may be blended with magnesium stearate and the rest of the starch. Then the mixture may be then compressed in a tableting machine to give tablets containing 10 mg of active compound.

EXAMPLE V

Tablets may be prepared by the method of the previous Example. The tablets may be enteric-coated in a conventional manner using a solution of 20% cellulose acetate phthalate and 3% diethyl phthalate in ethanol:dichloromethane (in a 1:1 ratio by volume) as solvent.

EXAMPLE W

In the preparation of capsules, 10 parts by weight of active compound and 240 parts by weight of lactose may be de-aggregated and blended. The mixture may be filled into hard gelatin capsules, each capsule containing 10 mg active compound.

EXAMPLE X

In the preparation of capsules, 50 parts by weight of active compound, 300 parts by weight of lactose and 3 parts by weight of magnesium stearate may be de-aggregated and blended. The mixture may be filled into hard gelatin capsules, each capsule containing 50 mg of active ingredient.

EXAMPLE Y

In the preparation of suppositories, 100 parts by weight of active compound may be incorporated in 1300 parts by weight of semi-synthetic glycerides as the suppository base and the mixture may be formed into suppositories each containing 100 mg of active ingredient.

EXAMPLE Z

An ointment may be formed by incorporating 0.1 g of the active compound into a base of white soft paraffin (9.9 g) by thorough homogenization until the drug is evenly distributed. The ointment (10 g) may be packed into amber jars with screw-capped lined lids.

We claim:

1. Compounds of formula II

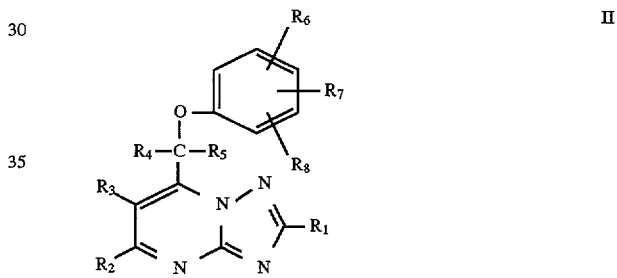

which includes pharmaceutically acceptable salts thereof and stereoisomers thereof
in which:

$R_1$ represents H or one of the following groups (optionally substituted with one or more of halo, cyano, hydroxy or amino): $C_{1-6}$alkyl, $C_{1-6}$alkoxy or $C_{1-6}$alkanoyl;

$R_2$ and $R_3$ independently represent H or one of the following groups (optionally substituted with one or more of halo, cyano, hydroxy or amino): $C_{1-6}$alkyl, $C_{1-6}$alkoxy, $C_{1-6}$alkanoyl, $C_{1-6}$alkylthio, $C_{1-6}$alkylsulphinyl or $C_{1-6}$alkylsulphonyl;

$R_4$ and $R_5$ independently represent H, $C_{1-6}$alkyl or $R_4$ and $R_5$ combined together with the carbon atom to which they are attached represent $C_{3-6}$cycloalkylidene (each alkyl or cycloalkylidene being optionally substituted with one or more of halo, cyano, hydroxy, amino or $C_{1-6}$alkyl); and $R_6$, $R_7$ and $R_8$ independently represent H, halo, hydroxy, mercapto, cyano or one of the following groups (optionally substituted with one or more of halo, cyano, hydroxy or amino; and any nitrogen atom being optionally substituted with one or more $C_{1-6}$alkyl); $C_{1-6}$alkyl, $C_{1-6}$alkanoyl, $C_{1-6}$alkoxy, $C_{2-6}$alkoxycarbonyl, carboxy, $C_{1-6}$alkanoyloxy, $C_{1-6}$alkylthio, $C_{1-6}$alkylsulphinyl, $C_{1-6}$alkylsulphonyl, $C_{1-6}$alkylsulphonylamino, sulphamoyl, carbamoyl, $C_{2-6}$alkylcarbamoyl or $C_{1-6}$alkanoylamino;

with the proviso that if

R$_1$, R$_2$, R$_3$, R$_4$ and R$_8$ are all H;

R$_5$ is methyl and either:

R$_6$ and R$_7$ are both H; or:

R$_6$ is 4-chloro and R$_7$ is H or 2-chloro;

the compound of formula II is not a racemate.

2. Compounds of formula II as claimed in claim 1, in which:

R$_1$, R$_2$, R$_3$, R$_4$ and R$_5$ independently represent H or C$_{1-4}$alkyl; and R$_6$, R$_7$ and R$_8$ independently represent H, halo, cyano or one of the following groups (optionally substituted with one or more halo): C$_{1-4}$alkyl, C$_{1-4}$alkoxy, C$_{1-4}$alkanoyl, C$_{1-4}$alkylthio, C$_{1-4}$alkylsulphinyl, or C$_{1-4}$alkylsulphonyl.

3. Compounds of formula II, as claimed in claim 1, in which:

R$_1$, R$_2$ and R$_3$ independently represent H or methyl;

R$_4$ and R$_5$ independently represent H, methyl or ethyl; and

R$_6$, R$_7$ and R$_8$ independently represent H, fluoro, chloro, bromo, cyano, trifluoromethyl, methoxy, trifluoromethoxy, acetyl, methylthio, ethylthio, methylsulphinyl or methylsulphonyl.

4. Compounds of formula II as claimed in claim 1 selected from:

7-[1-(4-fluorophenoxy)ethyl]-1,2,4-triazolo[1,5-a]pyrimidine;

7-[1-(4-chlorophenoxy)ethyl]-1,2,4-triazolo[1,5-a]pyrimidine;

7-[1-(4-bromophenoxy)ethyl]-1,2,4-triazolo[1,5-a]pyrimidine;

7-[1-(4-cyanophenoxy)ethyl]-1,2,4-triazolo[1,5-a]pyrimidine;

7-[1-(4-trifluoromethylphenoxy)ethyl]-1,2,4-triazolo[1,5-a]pyrimidine;

7-[1-(4-methoxyphenoxy)ethyl]-1,2,4-triazolo[1,5-a]pyrimidine;

7-[1-(4-trifluoromethoxyphenoxy)ethyl]-1,2,4-triazolo[1,5-a]pyrimidine;

7-[1-(4-acetylphenoxy)ethyl]-1,2,4-triazolo[1,5-a]pyrimidine;

7-{1-[4-(methylthio)phenoxy]ethyl}-1,2,4-triazolo[1,5-a]-pyrimidine;

7-[1-(4-methylsulphinylphenoxy)ethyl]-1,2,4-triazolo[1,5-a]pyrimidine;

7-[1-(4-methylsulphonylphenoxy)ethyl]-1,2,4-triazolo[1,5-a]-pyrimidine;

7-{1-[4-(ethylthio)phenoxy]ethyl}-1,2,4-triazolo[1,5-a]pyrimidine;

7-[1-(3-chlorophenoxy)ethyl]-1,2,4-triazolo [1,5-a]pyrimidine;

7-[1-(2,4-difluorophenoxy)ethyl]-1,2,4-triazolo[1,5-a]pyrimidine;

7-[1-(2,4-dichlorophenoxy)ethyl]-1,2,4-triazolo [1,5-a]pyrimidine;

7-[1-(3,4-dichlorophenoxy)ethyl]-1,2,4-triazolo[1,5-a]pyrimidine;

7-[1-(2-chloro-4-fluorophenoxy)ethyl]-1,2,4-triazolo[1,5-a]pyrimidine;

7-[1-(4-chlorophenoxy)ethyl]-2-methyl-1,2,4-triazolo[1,5-a]pyrimidine;

7-(4-chlorophenoxymethyl)-1,2,4-triazolo[1,5-a]pyrimidine;

7-[1-(4-chlorophenoxy)-1-methylethyl]-1,2,4-triazolo[1,5-a]pyrimidine; and

7-[1-(4-chlorophenoxy)propyl]-1,2,4-triazolo[1,5-a]pyrimidine.

5. Compounds of formula II as claimed in claim 1 selected from:

(+)-7-[1-fluorophenoxy)ethyl]-1,2,4-triazolo[1,5-a]pyrimidine;

(−)-7-[1-fluorophenoxy)ethyl]-1,2,4-triazolo[1,5-a]pyrimidine;

(+)-7-[1-(4-chlorophenoxy)ethyl]-1,2,4-triazolo[1,5-a]pyrimidine; and (−)-7-[1-(4-chlorophenoxy)ethyl]-1,2,4-triazolo[1,5-a]pyrimidine.

6. Pharmaceutical compositions comprising a therapeutically effective amount of one or more compound or compounds of formula I

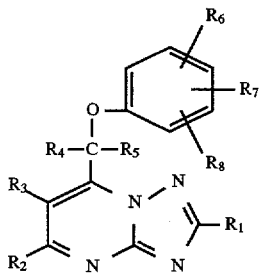

which includes pharmaceutically acceptable salts thereof and stereoisomers thereof in which:

R$_1$ represents H or one of the following groups (optionally substituted with one or more of halo, cyano, hydroxy or amino): C$_{1-6}$alkyl, C$_{1-6}$alkoxy or C$_{1-6}$alkanoyl;

R$_2$ and R$_3$ independently represent H or one of the following groups (optionally substituted with one or more of halo, cyano, hydroxy or amino): C$_{1-6}$alkyl, C$_{1-6}$alkoxy, C$_{1-6}$alkanoyl, C$_{1-6}$alkylthio, C$_{1-6}$alkylsulphinyl or C$_{1-6}$alkylsulphonyl;

R$_4$ and R$_5$ independently represent H, C$_{1-6}$alkyl or R$_4$ and R$_5$ combined together with the carbon atom to which they are attached represent C$_{3-6}$cycloalkylidene (each alkyl or cycloalkylidene being optionally substituted with one or more of halo, cyano, hydroxy, amino or C$_{1-6}$alkyl);

R$_6$, R$_7$ and R$_8$ independently represent H, halo, hydroxy, mercapto, cyano or one of the following groups (optionally substituted with one or more of halo, cyano, hydroxy or amino; and any nitrogen atom being optionally substituted with one or more C$_{1-6}$alkyl): C$_{1-6}$alkyl, C$_{1-6}$alkanoyl, C$_{1-6}$alkoxy, C$_{2-6}$alkoxycarbonyl, carboxy, C$_{1-6}$alkanoyloxy, C$_{1-6}$alkylthio, C$_{1-6}$alkylsulphinyl, C$_{1-6}$alkylsulphonyl, C$_{1-6}$alkylsulphonylamino, sulphamoyl, carbamoyl, C$_{2-6}$alkylcarbamoyl or C$_{1-6}$alkanoylamino;

together with a pharmaceutically acceptable diluent or carrier.

7. A pharmaceutical composition as claimed in claim 6, comprising a therapeutically effective amount of one or more compound or compounds of formula I in which:

R$_1$, R$_2$, R$_3$, R$_4$ and R$_5$ independently represent H or C$_{1-4}$alkyl; and R$_6$, R$_7$ and R$_8$ independently represent H, halo, cyano or one of the following groups (optionally substituted with one or more halo): $C_{1-4}$alkyl, $C_{1-4}$alkoxy, $C_{1-4}$alkanoyl, $C_{1-4}$alkylthio, $C_{1-4}$alkylsulphinyl or $C_{1-4}$alkylsulphonyl.

8. A pharmaceutical composition as claimed in claim 6, comprising a therapeutically effective amount of one or more compound or compounds of formula I, in which:

$R_1$, $R_2$ and $R_3$ independently represent H or methyl;

$R_4$ and $R_5$ independently represent H, methyl or ethyl; and $R_6$, $R_7$ and $R_8$ independently represent H, fluoro, chloro, bromo, cyano, trifluoromethyl, methoxy, trifluoromethoxy, acetyl, methylthio, ethylthio, methylsulphinyl or methylsulphonyl.

9. A pharmaceutical composition as claimed in claim 6, comprising a therapeutically effective amount of one or more compound or compounds of formula I selected from:

7-[1-(4-fluorophenoxy)ethyl]-1,2,4-triazolo[1,5-a]pyrimidine;

7-[1-(4-chlorophenoxy)ethyl]-1,2,4-triazolo[1,5-a]pyrimidine;

7-[1-(4-bromophenoxy)ethyl]-1,2,4-triazolo[1,5-a]pyrimidine;

7-[1-(4-cyanophenoxy)ethyl]-1,2,4-triazolo[1,5-a]pyrimidine;

7-[1-(4-trifluoromethylphenoxy)ethyl]-1,2,4-triazolo[1,5-a]pyrimidine;

7-[1-(4-methoxyphenoxy)ethyl]-1,2,4-triazolo[1,5-a]pyrimidine;

7-[1-(4-trifluoromethoxyphenoxy)ethyl]-1,2,4-triazolo[1,5-a]pyrimidine;

7-[1-(4-acetylphenoxy)ethyl]-1,2,4-triazolo[1,5-a]pyrimidine;

7-{1-[4-(methylthio)phenoxy]ethyl}-1,2,4-triazolo[1,5-a]-pyrimidine;

7-[1-(4-methylsulphinylphenoxy)ethyl]-1,2,4-triazolo[1,5-a]pyrimidine;

7-[1-(4-methylsulphonylphenoxy)ethyl]-1,2,4-triazolo[1,5-a]-pyrimidine;

7-{1-[4-(ethylthio)phenoxy]ethyl}-1,2,4-triazolo[1,5-a]pyrimidine;

7-[1-(3-chlorophenoxy)ethyl]-1,2,4-triazolo[1,5-a]pyrimidine;

7-[1-(2,4-difluorophenoxy)ethyl]-1,2,4-triazolo[1,5-a]pyrimidine;

7-[1-(2,4-dichlorophenoxy)ethyl]-1,2,4-triazolo [1,5-a]pyrimidine;

7-[1-(3,4-dichlorophenoxy)ethyl]-1,2,4-triazolo[1,5-a]pyrimidine;

7-[1-(2-chloro-4-fluorophenoxy)ethyl]-1,2,4-triazolo[1,5-a]pyrimidine;

7-[1-(4-chlorophenoxy)ethyl]-2-methyl-1,2,4-triazolo[1,5-a]pyrimidine;

7-(4-chlorophenoxymethyl)-1,2,4-triazolo[1,5-a]pyrimidine;

7-[1-(4-chlorophenoxy)-1-methylethyl]-1,2,4-triazolo[1,5-a]pyrimidine; and

7-[1-(4-chlorophenoxy)propyl]-1,2,4-triazolo[1,5-a]pyrimidine.

10. A pharmaceutical composition as claimed in claim 6, comprising a therapeutically effective amount of one or more compound or compounds of formula I selected from:

(+)-7-[1-(4-fluorophenoxy)ethyl]-1,2,4-triazolo[1,5-a]pyrimidine;

(−)-7-[1-(4-fluorophenoxy)ethyl]-1,2,4-triazolo[1,5-a]pyrimidine;

(+)-7-[1-(4-chlorophenoxy)ethyl]-1,2,4-triazolo[1,5-a]pyrimidine; and (−)-7-[1-(4-chlorophenoxy)ethyl]-1,2,4-triazolo[1,5-a]pyrimidine.

11. A method of treating seizures, epilepsy, stroke, brain trauma, head injuries and hemorrhage in animals, including human beings, which comprises administering a therapeutically effective amount of a member selected from the group consisting of a compound of formula I as represented in claim 6 and a pharmaceutical composition as defined in claim 6.

12. A process for the preparation of compounds of formula II of claim 1, comprising:

Coupling alcohols of formula XVII

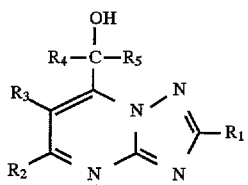

with phenols of formula XVIII

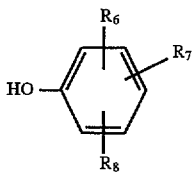

in the presence of a suitable coupling agent.

* * * * *